United States Patent
Westerlund et al.

(10) Patent No.: US 11,722,752 B2
(45) Date of Patent: Aug. 8, 2023

(54) RESOURCE SEGMENTATION TO IMPROVE DELIVERY PERFORMANCE

(71) Applicant: TELEFONAKTIEBOLAGET LM ERICSSON (PUBL), Stockholm (SE)

(72) Inventors: Magnus Westerlund, Upplands Väsby (SE); Beatriz Grafulla-González, Solna (SE); Göran Eriksson, Norrtälje (SE)

(73) Assignee: TELEFONAKTIEBOLAGET LM ERICSSON (PUBL), Stockholm (SE)

( * ) Notice: Subject to any disclaimer, the term of this patent is extended or adjusted under 35 U.S.C. 154(b) by 565 days.

(21) Appl. No.: 16/348,814

(22) PCT Filed: Nov. 10, 2017

(86) PCT No.: PCT/EP2017/078926
§ 371 (c)(1),
(2) Date: May 9, 2019

(87) PCT Pub. No.: WO2018/087309
PCT Pub. Date: May 17, 2018

(65) Prior Publication Data
US 2020/0186896 A1    Jun. 11, 2020

Related U.S. Application Data

(60) Provisional application No. 62/420,120, filed on Nov. 10, 2016.

(51) Int. Cl.
*H04N 21/845* (2011.01)
*H04N 21/8352* (2011.01)
(Continued)

(52) U.S. Cl.
CPC ......... *H04N 21/8456* (2013.01); *A61B 34/76* (2016.02); *A61B 90/37* (2016.02);
(Continued)

(58) Field of Classification Search
CPC ............ H04N 21/8456; H04N 21/8352; H04L 65/4084; H04L 65/602; H04L 65/607; H04L 65/80
See application file for complete search history.

(56) References Cited

U.S. PATENT DOCUMENTS

| 8,166,191 B1 | 4/2012 | Swaminathan et al. |
| 2009/0254933 A1* | 10/2009 | Gupta ............... H04H 20/14 725/14 |

(Continued)

FOREIGN PATENT DOCUMENTS

| CN | 102137089 A | 7/2011 |
| CN | 103747365 A | 4/2014 |

(Continued)

OTHER PUBLICATIONS

International Search Report and the Written Opinion of the International Searching Authority, issued in corresponding International Application No. PCT/EP2017/078926, dated Jan. 31, 2018, 13 pages.

(Continued)

*Primary Examiner* — John A Follansbee
*Assistant Examiner* — Raqiul A Choudhury
(74) *Attorney, Agent, or Firm* — Rothwell, Figg, Ernst & Manbeck, P.C.

(57) ABSTRACT

A flexible approach to segmenting a resource (e.g., a media resource, such as a media segment, or other resource, such as a resource normally fetched or pushed using general file transfer protocols like HTTP) into a plurality of fragments. By employing such an approach, the delay until the resource can be utilized at the client side is reduced. Certain embodiments are provided which apply the flexible segmentation approach to ISOBMFF media segments for video streaming, such as would be used with Live DASH streaming.

19 Claims, 13 Drawing Sheets

(51) Int. Cl.
| | |
|---|---|
| *H04N 21/84* | (2011.01) |
| *H04L 65/70* | (2022.01) |
| *H04L 65/75* | (2022.01) |
| *H04L 65/80* | (2022.01) |
| *A61B 34/00* | (2016.01) |
| *A61B 90/00* | (2016.01) |
| *H04L 65/612* | (2022.01) |
| *A61B 34/37* | (2016.01) |
| *A61B 17/00* | (2006.01) |

(52) U.S. Cl.
CPC .......... *H04L 65/612* (2022.05); *H04L 65/70* (2022.05); *H04L 65/762* (2022.05); *H04L 65/80* (2013.01); *H04N 21/8352* (2013.01); *H04N 21/84* (2013.01); *A61B 34/37* (2016.02); *A61B 2017/00022* (2013.01); *A61B 2017/00115* (2013.01); *A61B 2090/065* (2016.02); *A61B 2090/365* (2016.02)

(56) References Cited

U.S. PATENT DOCUMENTS

| | | |
|---|---|---|
| 2010/0235528 A1 | 9/2010 | Bocharov et al. |
| 2012/0137015 A1 | 5/2012 | Sun |
| 2012/0320154 A1 | 12/2012 | Berger et al. |
| 2013/0188932 A1 | 7/2013 | Hartley |
| 2013/0226930 A1 | 8/2013 | Arngren et al. |
| 2013/0246643 A1 | 9/2013 | Luby et al. |
| 2013/0291082 A1* | 10/2013 | Giladi ............... H04L 63/08 726/7 |
| 2014/0032777 A1 | 1/2014 | Yuan et al. |
| 2014/0089990 A1 | 3/2014 | van Deventer et al. |
| 2014/0359140 A1* | 12/2014 | Shankarraman ...... H04L 65/601 709/227 |
| 2015/0256600 A1* | 9/2015 | Dakhane ............. H04L 65/60 709/203 |
| 2016/0261665 A1 | 9/2016 | Stockhammer et al. |
| 2016/0294898 A1 | 10/2016 | Wheelock |
| 2016/0301957 A1 | 10/2016 | McCarthy et al. |
| 2016/0337424 A1* | 11/2016 | Mandyam ........ H04N 21/26258 |
| 2016/0337426 A1* | 11/2016 | Shribman ............ H04L 65/608 |
| 2017/0223424 A1 | 8/2017 | Degrange |
| 2018/0115791 A1 | 4/2018 | Resch |

FOREIGN PATENT DOCUMENTS

| | | |
|---|---|---|
| CN | 103814562 A | 5/2014 |
| CN | 103858440 A | 6/2014 |
| CN | 104137564 A | 11/2014 |
| CN | 105659240 A | 6/2016 |
| CN | 105659623 A | 6/2016 |
| CN | 106034242 A | 10/2016 |
| JP | 2014-529970 A | 11/2014 |
| JP | 2015-501090 A | 1/2015 |
| JP | 2015-519814 A | 7/2015 |
| JP | 2015519813 A | 7/2015 |
| JP | 2015-208018 A | 11/2015 |
| WO | 2013163448 A1 | 10/2013 |
| WO | 2015064383 A1 | 5/2015 |

OTHER PUBLICATIONS

Kofler et al. "Implications of the ISO Base Media File Format on Adaptive HTTP Streaming of H.264/SVC" Consumer Communications and Networking Conference (CCNC), 2012 IEEE, Jan. 14, 2012, pp. 549-553.

M. Thomson "Content-Signature Header Field for HTTP draft-thomson-http-content-signature-00" Internet—Draft, Jul. 2, 2015, 6 pages.

M. Thomson "Merkle Integrity Content Encoding draft-thomson-http-mice-01" Network Working Group, Internet—Draft, Jun. 29, 2016, 10 pages.

J. Reschke et al. "'Out-Of-Band' Content Coding for HTTP draft-reschke-http-oob-encoding-08" Network Working Group, Internet—Draft, Sep. 26, 2016, 20 pages.

A. Barth "The Web Origin Concept" Internet Engineering Task Force (IETF), Request for Comments: 6454, Dec. 2011, 17 pages.

R. Pantos et al. "HTTP Live Streaming draft-pantos-http-live-streaming-20" Informational, Internet—Draft, Sep. 20, 2016, 47 pages.

International Standard "Information technology—Dynamic adaptive streaming over HTTP (DASH)—Part 1: Media presentation description and segment formats" ISO/IEC 23009-1, Second edition, May 15, 2014,152 pages.

R. Fielding et al. "Hypertext Transfer Protocol (HTTP/1.1): Message Syntax and Routing" Internet Engineering Task Force (IETF), Request for Comments: 7230, Jun. 2014, 89 pages.

International Standard "Information technology—Coding of audio-visual objects—Part 12: ISO base media file format" ISO/IEC 14496-12, 2012, 190 pages.

M. Thomson "Encrypted Content-Encoding for HTTP draft-ietf-httpbis-encryption-encoding-03" HTTP Working Group, Internet—Draft, Oct. 9, 2016, 19 pages.

M. Nottingham et al. "HTTP Alternative Services" Internet Engineering Task Force (IETF), Request for Comments: 7838, Apr. 2016, 20 pages.

Qualcomm Incorporated "MI-EMO: Guidelines for out of order sending of movie fragments" 3GPP TSG-SA4 #81, S4-141201, Aug. 3-7, 2014, 6 pages.

3GPP 3rd Generation Partnership Project; Technical Specification Group Services and System Aspects; Transparent end-to-end packet switched streaming service (PSS); 3GPP file format (3GP) (Release 13), 3GPP TS 26.244 V13.4.1 (Sep. 2016), 67 pages.

* cited by examiner

RESOURCE SEGMENTATION TO IMPROVE DELIVERY PERFORMANCE

CROSS REFERENCE TO RELATED APPLICATION(S)

This application is a 35 U.S.C. § 371 National Phase Entry Application from PCT/EP2017/078926, filed Nov. 10, 2017, designating the United States, and also claims the benefit of U.S. Provisional Application No. 62/420,120, filed Nov. 10, 2016, the disclosures of which are incorporated herein by reference in their entirety.

TECHNICAL FIELD

Disclosed are embodiments for segmenting resources, such as media segments used in live streaming.

BACKGROUND

Current Streaming Approaches

Current approaches for live and video-on-demand adaptive bit-rate streaming primarily rely on the Hypertext Transfer Protocol (HTTP) (see, e.g., [HTTP]). In these approaches, a client (also referred to as a User Agent or UA) may use HTTP to retrieve a multitude of media segments, each of which contains media samples (i.e., audio samples and/or video samples). These media segments are in accordance to certain formats (e.g., ISOBMFF), enabling the client to parse the media segment, decode the media samples, and ultimately to play the media to a user of the client. That is, after having retrieved a media segment, the client is able to parse and render the contents of the media segment to the user.

Under these current approaches, there is a higher layer that provides information about the location of the individual media segments, including potentially different representations for such media segments (e.g., different representations having different qualities of encoding). Two dominant solutions are used: (1) HTTP Live Streaming (HLS) (see, e.g., [HLS]) and (2) Dynamic adaptive streaming over HTTP (DASH) (see, e.g., [DASH]). Both of these solutions use a manifest file that describes the different media segments and their bit-rates so that the streaming client can determine which media segment to retrieve. While there are several different media segment formats, both HLS and DASH support the ISO Base Media File Format (ISOBMFF) (see, e.g., [ISOBMFF]).

Media Segment Formats

ISOBMFF is a flexible media container file format. It consists of structures that are called boxes. A box may include an identifier and a length field and may include metadata that defines what the box contains. A box may contain one or more boxes of other types. Specific formats, such as for certain types of media or use cases, may place additional restrictions on the generic ISOBMFF structure (e.g., define requirements on the media file, specify which types of boxes the file must contain). DASH defines several types of segments using the ISOBMFF file format, such as Initialization Segments and Media Segments. An Initialization Segment may contain information necessary to decode Media Segments. But only the Media Segments contain the media samples. Each Media Segment contains a moof box and an mdat box.

The MOOF box contains a track fragment (traf) box that contains a Track Run Box (trun). The trun box documents a contiguous set of media samples that is stored inside the mdat box. So for each media sample at least its data size, and the duration of the media sample is provided. This enables the media samples to be stored continuous after each other inside the mdat box. The moof box is stored before the mdat box.

Distribution of Work Load

There is ongoing work on an out-of-band (OOB) content encoding mechanism for HTTP (see, e.g., [OOB]). This OOB mechanism enables a server to redirect the serving of the HTTP response body to another trust domain. This may be used, for example, to securely redirect to Content Distribution Network (CDN) nodes, edge servers or third party caches/proxies without violating the same origin policies, having good privacy properties, and enabling greater flexibility in the content distribution when all individual HTTP requests are done in the context of Transport Layer Security (TLS) connections.

HTTP Alternative services (see, e.g., [alt-services]) are another method for redirecting responses to request to other network location and possibly other delivery protocols. Using HTTP Alternative services, the resource identity is separated from the location of the resource. However, this redirect applies to the whole origin, and cannot be performed on an individual resource level.

Resource Verification

In the HTTP context there are several different mechanisms being developed for protecting and verifying the integrity of the body of a requested resource (e.g., a requested media segment). One proposal is a signature for the response body (see, e.g., [CONTENTSIG]). Another approach is the application of Advanced Encryption Standard (AES) Galois Counter Mode (GCM), or AES GCM, which allows for confidentiality and integrity verification of message bodies as a content encoding (see, e.g., [aesgcm]). Another proposal is Merkle Integrity Content Encoding, or MICE, that provides integrity verification using fixed size records (see, e.g., [MICE]). With MICE, each record can be verified as it arrives, allowing progressive verification on the receiver side, given that the previous record was verified, or that the correct hash for that record is known for the entity performing verification.

REFERENCES

[CONTENTSIG] Thomson, M., "Content-Signature Header Field for HTTP", draft-thomson-http-content-signature-00 (work in progress), July 2015.

[MICE] Thomson, M., "Merkle Integrity Content Encoding", draft-thomson-http-mice-01 (work in progress), June 2016.

[OOB] J. Reschke, and S. Loreto, "'Out-Of-Band' Content Coding for HTTP", draft-reschke-http-oob-encoding-08 (work in progress), September 2016.

[RFC6454], A. Barth, "The Web Origin Concept", RFC 6454, December 2011.

[HLS] R. Pantos, and W. May, "HTTP Live Streaming", draft-pantos-http-live-streaming-20 (work in progress), September 2016.

[DASH] "Information technology—Dynamic adaptive streaming over HTTP (DASH)—Part 1: Media presentation description and segment formats", ISO/IEC 23009-1:2014, May 2014.

[HTTP] R. Fielding, J. Reschke, "Hypertext Transfer Protocol (HTTP/1.1): Message Syntax and Routing", IETF RFC 7230, June 2014.

[ISOBMFF] "Information technology—Coding of audio-visual objects—Part 12: ISO base media file format", ISO/IEC 14496-12, July 2012.
[aesgcm] M. Thomson, "Encrypted Content-Encoding for HTTP", IETF draft-ietf-httpbis-encryption-encoding-03 (work in progress), October 2016.
[alt-services] M. Nottingham, et al, "HTTP Alternative Services", IETF RFC 7838, April 2016.
[S4-141201] 3GPP TSG-SA4 #81, "MI-EMO: Guidelines for out of order sending of movie fragments", http://www.3gpp.org/ftp/tsg_sa/wg4_codec/TSGS4_81/Docs/S4-141201.zip, August 2014.

SUMMARY

Problems with Existing Solutions

One common way to deliver live streaming is to use DASH with the ISO base Media File Format (ISO BMFF). The ISO BMFF Media Segment format specifies that the moof box (i.e. the box that contains metadata (e.g., length and position) for media samples included in the moof's corresponding mdat box) precedes the mdat box. This requirement prevents an encoder from generating the entire moof prior to the encoder having completed the encoding of the corresponding media samples. This, therefore, introduces a delay. The delay may be measured as $T_{source\_to\_playback}$ (delay from when the encoder begins generating the media samples for a media segment to when a client may begin playback). This delay is important to the user, as it affects how soon a media segment is available to be watched. $T_{source\_to\_playback}$ may further be measured as a sum of $T_{source\_to\_reception}$ (delay from when the encoder begins encoding a media segment to when the encoder may provide the media segment to a receiving entity) and $T_{reception\_to\_playback}$ (delay from when the receiving entity first begins receiving the media segment to when playback may begin). Requiring the length and position of media samples to be written prior to the data part in the file format (e.g., the moof cannot be completed until all the media samples are generated) therefore increases $T_{source\_to\_playback}$ because it increases $T_{source\_to\_reception}$. This delay increases with the length of the media segment (typically about 2-10 seconds).

One known approach to deal with this delay, i.e., to minimize the above-mentioned delay, is to create multiple ISOBMFF "movie fragments" for a particular media segment. That is, create a media segment comprising a sequence of moof/mdat box pairs. For example, a media segment may contain a first movie fragment (i.e., a first moof box followed by a first mdat box) and a second movie fragment (i.e., a second moof box followed by a second mdat box). This enables transmission of a movie fragment as soon the movie fragment has been created. This can decrease the delay, since the delay depends on the length of the fragment, and this approach creates more fragments each having a smaller length. However, in addition to decreasing the delay, this approach also increases the overhead. Further, the approach creates additional random access points (defined according to the standard as points where decoding and continuous playback can begin without relying on any previous data in the segment). The approach can also effect the video encoding, as the frequency of random access points negatively affects the efficiency of the encoding (e.g., for video encoding, it may result in a sub-optimal number of I-frames).

The above-described approach also suffers from additional problems. For example, the approach further suffers from not allowing random access when verification of resource (e.g., media segment) integrity is required. Due to the properties of integrity mechanism, unrestricted random access is not be possible. Notwithstanding, the above-described approach does not allow any random access points within a resource, except for the beginning of the resource. Providing for additional random access points would provide benefits, such as enabling late joiners to live streams, or seeking within a larger video sequence, or access a particular random access point within a media segment.

Further problems arise when employing the above-described approach with Out of Band (OOB) encoding, particularly with HTTP resource retrieval. For example, the above-described approach, if using AES GCM for verification, requires the whole resource to be retrieved in order to verify the integrity of the resource. This affects the shortest time between content ingestion until a receiving client can play out the content, i.e., time between encoding and client play back (i.e., $T_{source\_to\_playback}$). At the ingestion (encoding) side, the content needs to be completely ingested before integrity verifying hashes can be calculated. That is because such hashes are computed over the entire resource. Then, at the receiver (decoding) side, the client that is verifying what it has received with what was intended to be sent, must first receive all the content the integrity hash was calculated over, i.e., the entire resource.

Another known approach, besides AES GCM, is Merkle Integrity Content Encoding (MICE). However, even if this is used, there are still shortcomings. MICE partially addresses some problems with AES GCM, because it allows the receiver to perform progressive verification of the resource on a per-block basis, as each block has completed delivery (where the block is a smaller unit than the resource). Thus, the above-mentioned client side delay depends on the block size used and its alignment with underlying content structures, rather than the size of the whole resource. However, MICE does not address the above-mentioned server side delay, as the approach still requires that the encoder have the last part of the resource when calculating the integrity protection and adding the hash chain to the content.

Known integrity verification mechanisms do not work effectively with content that is dynamically generated. That is because such mechanisms tend to require the encoder to know the whole resource to be verified. Although TLS or SSL may be used with Chunked Transfer encoding, and it may be possible to verify data at the transport-level, when data is being sent by a single server or trust domain, that solution is not viable when multiple domains are sending out information, such as delivery models like OOB that depend on integrity verification of resources from out of band servers.

Brief Summary of Exemplary Proposed Embodiments

The present application describes a flexible approach to segmenting a resource (e.g., a media resource, such as a media segment, or other resource, such as a resource normally fetched or pushed using general file transfer protocols like HTTP) into a plurality of fragments. By employing such an approach, the delay until the resource can be utilized at the client side is reduced. Certain embodiments are provided which apply the flexible segmentation approach specifically to ISOBMFF media segments for video streaming, such as would be used with Live DASH streaming. These embodiments, by using the described flexible segmentation, can significantly reduce the delay between media samples becoming available on the server side until client side playback can begin (i.e., $T_{source\_to\_playback}$). In one embodiments, this is accomplished by using a file segmentation mechanism proposed here, which is capable of changing the order that parts of a resource are retrieved in (e.g., retrieval order may be different than logical order), as well as capable of enabling progressive fetch or push of parts of the resource as they are created by ingested media samples. The proposed resource segmentation mechanism also provides metadata to enable the receiver (client side) to utilize the resource fragments at an earlier stage than known solutions permit.

Another aspect of the present application relates to ensuring integrity of the full resource, as well as the resource fragments, while maintaining the properties and benefits provided by the flexible segmentation. For example, the described approach enables progressive integrity verification of individual chunks of a resource fragment. For resources that will be progressively generated, hashes over individual or groups of chunks (an integrity block) enable progressive verification. Using signatures over the individual hashes for each integrity block ensures that the hashes can be trusted, i.e., that they have been generated by a trusted entity. The segmentation solution including appropriate integrity protection is also capable of dealing with retrieval of resource segments from different trust domains, for example such that is created when using Out-of-Band Encoding or alternative services in HTTP. The solution also supports independent or different keys, or even independent or different protection mechanisms, for confidentiality protection of the individual resource segments, in order to fully support usage of multiple trust and security contexts.

In one aspect, there is provided a method for delivering a dynamically generated media stream to a client, the media stream comprising a plurality of media segments including a first media segment and a second media segment. The method includes: receiving an indication to send to the client a manifest file, wherein the manifest file comprises information describing the media segments. The method also includes sending, to the client, the manifest file in response to receiving the indication to send to the client the manifest file. The method also includes after sending the manifest file to the client, receiving an indication to send to the client the first media segment. And the method further includes, in response to the indication to send to the client the first media segment, sending, to the client, a segmentation map for the first media segment. The first media segment comprises an ordered set of fragments including a first fragment and a second fragment, and the segmentation map comprises: first fragment metadata comprising a first fragment identifier for use in accessing the first fragment from a server, second fragment metadata comprising a second fragment identifier for use in accessing the second fragment from a server, and ordering information identifying the ordering of the fragments within the set of fragments, including information indicating that the first fragment is ordered before the second fragment.

In some embodiments the method also includes receiving an indication to send to the client the first fragment, and sending, to the client, the first fragment in response to receiving the indication to send to the client the first fragment. In some embodiments, one or more of the indication to send to the client the manifest file, the indication to send to the client the first media segment, and the indication to send to the client the first fragment is generated by the server without client input. In some embodiments, the method also includes receiving a request to register the client to receive the media stream, prior to generating one or more of the indications.

In some embodiments, the indication to send to the client the first media segment is a request transmitted by the client, the request comprises information for identifying the first media segment, and the request further comprises an indicator indicating that the client supports a segmented mode. In some embodiments the method also includes determining to use the segmented mode to deliver the media segment, wherein the determination is based at least in part on the indicator. In some embodiments determining to use the segmented mode to deliver the first media segment is further based at least in part on whether the first media segment has been fully generated. In some embodiments a content of the manifest file is based on the indicator that the client supports the segmented mode, and the content of the manifest file that is based on the indicator comprises a hint regarding a time of resource availability for the plurality of media segments.

In some embodiments, the first fragment metadata further comprises one or more of: first dependency information for the first fragment, the first dependency information indicating that the availability of the first fragment to be delivered from the server is dependent on one or more other fragments of the set, first position information including one or more of: a length of the first fragment, a start position of the first fragment in the media segment, and an end position of the first fragment in the media segment, and first fragment-level security information for use in verifying the integrity of the first fragment.

In some embodiments the method also includes receiving a part of the first media segment from a source dynamically generating the media stream, wherein the part of the first media segment corresponds to at least one of a media sample and a media application data unit; and packetizing the part of the first media segment according to a format, wherein the format is ISO Base Media File Format. In some embodiments the first fragment comprises media samples, and the second fragment comprises metadata associated with the media samples.

In another aspect there is provided a method, performed by a client, for receiving a dynamically generated media stream, the media stream comprising a plurality of media segments including a first media segment and a second media segment. The method includes receiving a manifest file, wherein the manifest file comprises information for enabling the client to generate requests for the media segments. The method also includes processing the received manifest file, and, after processing the manifest file, receiving a segmentation map for the first media segment. The first media segment comprises an ordered set of fragments including a first fragment and a second fragment, and the segmentation map comprises: first fragment metadata comprising a first fragment identifier for use in accessing the first fragment from a first server, second fragment metadata comprising a second fragment identifier for use in accessing the second fragment from a server, and ordering information identifying the ordering of the fragments within the set of fragments, including information indicating that the first fragment is ordered before the second fragment. The method further includes receiving the first fragment.

In some embodiments the method also includes, prior to receiving the manifest file, sending a request for a manifest file and, after processing the manifest file and before receiving the segmentation map, sending a request identifying the first media segment. In some embodiments the request identifying the first media segment comprises an indicator indicating that the client supports a segmented mode.

In some embodiments one or more of the manifest file and first fragment is received by the client without the client sending a request. In some embodiments an application layer of the client sends a request for one or more of the manifest file and the first fragment to a local browser of the client, resulting in the application layer obtaining access to one or more of the manifest file and the first fragment.

In some embodiments a plurality of fragments for the first media segment is received by the client without the client sending a request. In some embodiments an application layer of the client assembles the first media segment based on the information in the segmentation map including the identity of the fragments, their provided offset in the file, or the sequence of fragments.

In some embodiments the method further includes verifying the first fragment, verifying the first media segment, and decoding and playing the first fragment. In some embodiments, the decoding and playing the first fragment occurs after verifying the first fragment and before verifying the first media segment.

In some embodiments the method also includes playing the first fragment, wherein playing the first fragment occurs prior to receiving other fragments of the media segment.

In another aspect there is provided a method for transmitting a media stream to a client, the media stream comprising a plurality of media segments including a first media segment and a second media segment, the first media segment comprising a plurality of media samples (e.g., mdat data such as audio and/or video samples) and media sample metadata (e.g., moof data). In some embodiments, the method includes transmitting to the client one or more of the plurality of media samples belonging to the first media segment; and transmitting to the client at least some of the media sample metadata belonging to the first media segment. The one or more of the plurality of media samples belonging to the first media segment are transmitted to the client before the at least some of the media sample metadata belonging to the first media segment is transmitted to the data. In some embodiments, the first media fragment further comprises media segment type information (e.g. STYP box), and the method further comprises transmitting the media segment type information belonging to the first media segment prior to transmitting the one or more of the plurality of media samples belonging to the first media segment.

Other embodiments and aspects are described below.

Advantages

The flexible segmentation mechanism can be used to improve delivery in several ways. For example, the delay until relevant fragments of the resource can be consumed by the receiving client may be reduced. Another example is that the approach fully supports the use edge servers or caches near to the receiving client, allowing resource fragments to be available in such edge servers or caches, and allowing the user to acquire any fragment from the closer or otherwise optimum provider, while other fragments may be retrieved from other instances where they are available. This results in improved delivery performance. Still another example is the ability to provide, and indicate to a user, redundancy in resource fragment storage. Still another advantage is the ability to retrieve or receive multiple fragments simultaneously from potentially different sources, which can result in improved delivery performance, making the encoding process faster.

Furthermore, the segmentation mechanism described in this application can be used to significantly improve the delay from content ingestion until playout ($T_{source\_to\_playback}$) for live streaming mechanisms like DASH and HLS, by intelligent segmentation of the media segments. This intelligent segmentation enables progressive delivery to the client of the individual fragments as encoded media samples are added to the segment by the packetizer. This also removes or at least reduces the delay in completing movie fragments in ISOBMFF files prior to being able to start transmission.

Furthermore, the segmentation mechanism described in this application can be used to improve the security model, e.g., resource verification and/or confidentiality. For example, the security model described is particularly advantageous when segmenting a resource into multiple fragments, where those fragments may be retrieved from multiple providers. The security model described in this application enables flexible usage of different integrity mechanisms suitable to the application's need when segmenting a resource into multiple fragments. For the live video streaming case, for example, a keyed- or signature-based integrity mechanism that handles flexible record sizes is advantageous. Such a mechanism allows individual chunks to be integrity protected, and allows delivered data to be immediately verified as correct and consumed without additional delay.

DETAILED DESCRIPTION

As used herein "a" should be interpreted to mean "one or more" unless indicated otherwise.

The present application describes exemplary embodiments for segmenting a resource (e.g., a resource that is intended to be delivered to a client from a server using a file delivery protocol like HTTP, FLUTE, or FCAST). Embodiments relate to the format of the segmented resource, methods and devices for performing the resource segmentation, and/or methods and devices for receiving/transmitting the segmented resource.

An exemplary solution for segmentation is based on providing a client a segmentation map for a given resource. In some embodiments, the client may specifically request the segmentation map or the given resource from a server.

Figure 1:
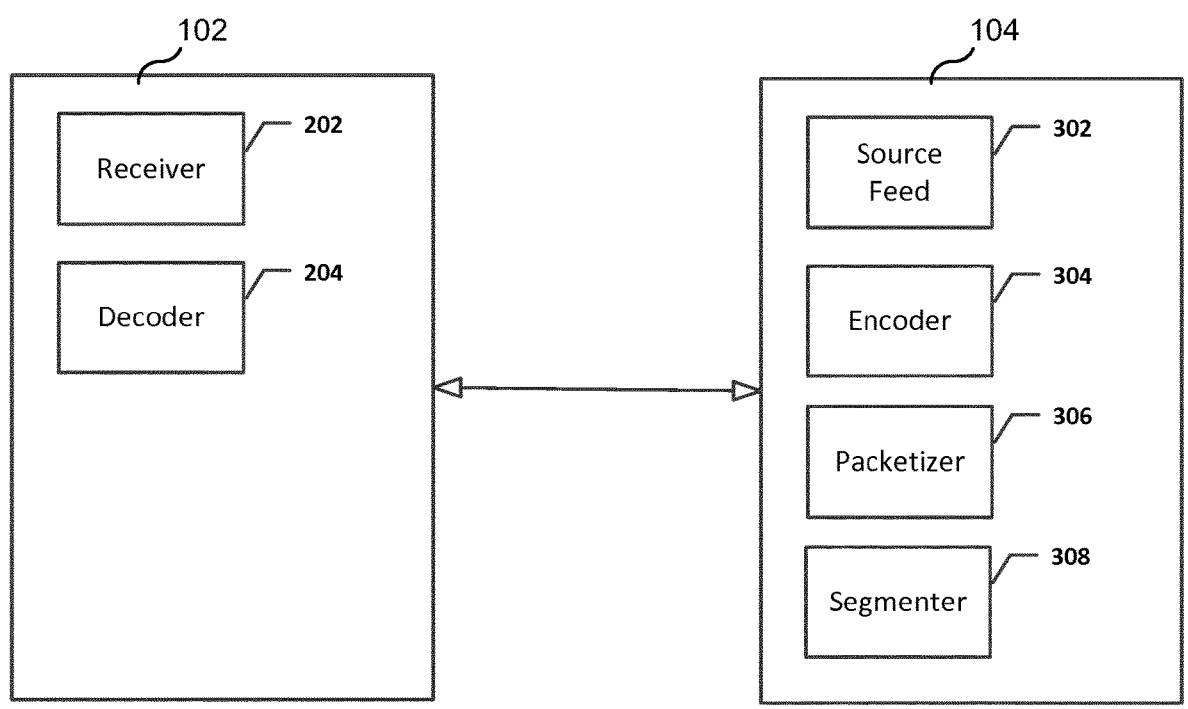
FIG. 1 illustrates a system according to exemplary embodiments.

As illustrated in FIG. 1, client 102 is in communication with server 104. In some embodiments, server 104 may be a traditional server; in other embodiments it may be a peer client in a peer-to-peer network.

A given resource is segmented into any number of fragments, suitable to the needs of the delivery or the application. The segmentation map can be updated for a given resource as more information about the individual fragments is determined. That is, the segmentation map may be created before having complete information about the individual fragments of the resource (i.e., before the resource is full specified).

According to exemplary embodiments, the segmentation map has some combination of the following described features.

The segmentation map indicates the order to assemble the individual fragments, either explicitly (e.g., by an index or sequence identifier), or implicitly (e.g., by an order imposed by a data structure implementing all or part of the segmentation map).

Each fragment has either a known or unknown length at the time of the segmentation map creation (including any updates made to the segmentation map). Thus, for each fragment, the segmentation map may indicate the length of the fragment (e.g., in bits) if the length is known at the time the map is created. If the length is not known, the file delivery protocol must be capable of indicating the fragment's final length, for example by using HTTP chunking or by closing the connection when the fragment has been fully delivered to the client by the server.

Each fragment has either a known or unknown position relative to the full resource (e.g., an offset) at the time of segmentation map creation. Thus, for each fragment, the segmentation map may indicate the offset of the fragment. If the position is unknown, a client or decoder can determine the position after receiving the segmentation map (e.g., when the position of the end of the prior fragment has been determined, or by receiving an updated segmentation map that includes the given fragment's position). One disadvantage to not knowing the position of the fragment is that it may lead to an additional move or copy operation (although, as described later, a memory-constrained client can order retrieval of fragments to minimize such moves or copies, based on dependency information provided in the segmentation map).

Each fragment has its own identifier (e.g., a locator, a name, etc.) to be used by the file retrieval protocol, for example an HTTP URL or the combination of an URL and the offset into that URL. Thus, for each fragment, the segmentation map may indicate the fragment's identifier. This enables the flexibility to use mechanisms like OOB to retrieve an individual fragment as its own resource or use multiple different servers for various reasons. Load balancing either in retrieval domain or for content processing reasons, can lead to performance improvements due to load spreading. The use of a locator for each fragment also enables redirecting to another delivery or retrieval protocol, either at URL level or using mechanisms like alternative services (see, e.g., [alt-services]).

Each fragment can have an individual security mechanism for confidentiality and integrity verification. Thus, for each fragment, the segmentation map may include information needed to perform the security operations associated with the fragment. This can be a hash over the data of the fragment, or indicate which certificate or key has been used for generating the hash or signature.

For each fragment, the segmentation map may include retrieval hints or dependency information indicating to the client in which order it should retrieve the fragments for optimal performance. One such optimization is to minimize the delay until delivery completes. Another hint may indicate that a particular fragment should be delivered after one or several other fragments have already been successfully delivered.

for each fragment, the segmentation map may include application-level hints associated with the resource media type enabling the receiving client to utilize the fragment prior to full delivery or on its own, rather than the full resource.

The segmentation map may also have resource-level properties. For example, to ensure that updates of the segmentation map are done at appropriate points, the segmentation map can include hints that when particular steps in the delivery and reassembly process have been reached an updated segmentation map can be requested.

Referring now to FIG. 1, a client 102 may be in communication with a server 104. As used herein a "server" can be a single computer that provides a service a set of computers that provides the service, where the set of computers may be co-located (e.g., a cluster of computers) or geographically dispersed. Client 102 may comprise a receiver 202 and a decoder 204. Receiver 202 comprises circuitry enabling client 102 to receive data from server 104 (e.g., a wired or wireless link, such as an RF receiver or Ethernet interface). Decoder 204 is operable to decode various media file formats. Server 104 may comprise a source feed 302, an encoder 304, a packetizer 306, and a segmenter 308. Source feed 302 may provide server 104 media data, such as live data as it is being generated (e.g., from a cable feed, a satellite feed, or other source), or data that is already generated and stored on server 104 or elsewhere. Encoder 304 is operable to encode media data received from source feed 302 into various media samples using for example H.264 or MPEG-4 Advanced Video coding (AVC). Packetizer 306 is operable to take media samples and put them into a packetized format suitable for sending over a packet-based protocol such as HTTP (e.g., packetizer 306 may put the media samples into ISO Base Media File Format by, for example, creating a media segment having an mdat box containing the media samples). Segmenter 308 is operable to take the packetized media and put it into a segmented format or deliver it in a segmented format (e.g., deliver it in accordance with a segmentation map.

Figure 2:
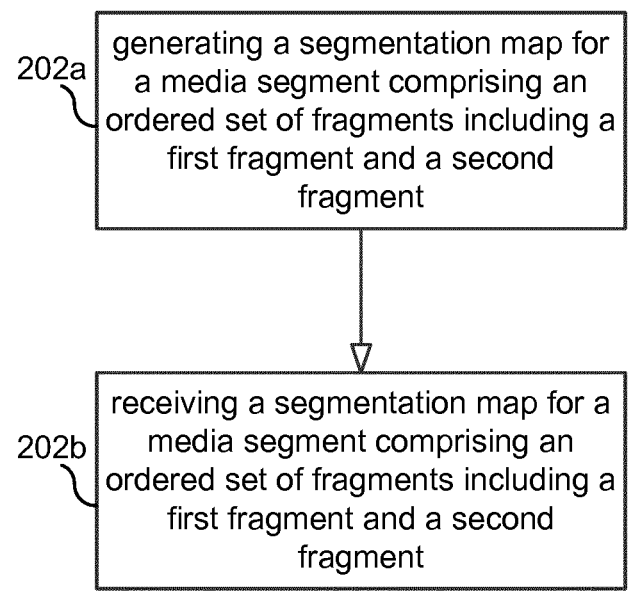
FIG. 2 illustrates a method according to an embodiment.

FIG. 2 illustrates a method according to an exemplary embodiment for generating and receiving a segmentation map. In some embodiments, a method comprises generating a segmentation map for a media segment comprising an ordered set of fragments including a first fragment and a second fragment (step 202a). In an embodiment, server 104 performs the generating a segmentation map step. In some embodiments, a method comprises receiving a segmentation map for a media segment comprising an ordered set of fragments including a first fragment and a second fragment (step 202b). In an embodiment, client 102 performs the receiving a segmentation map step.

Figure 3:
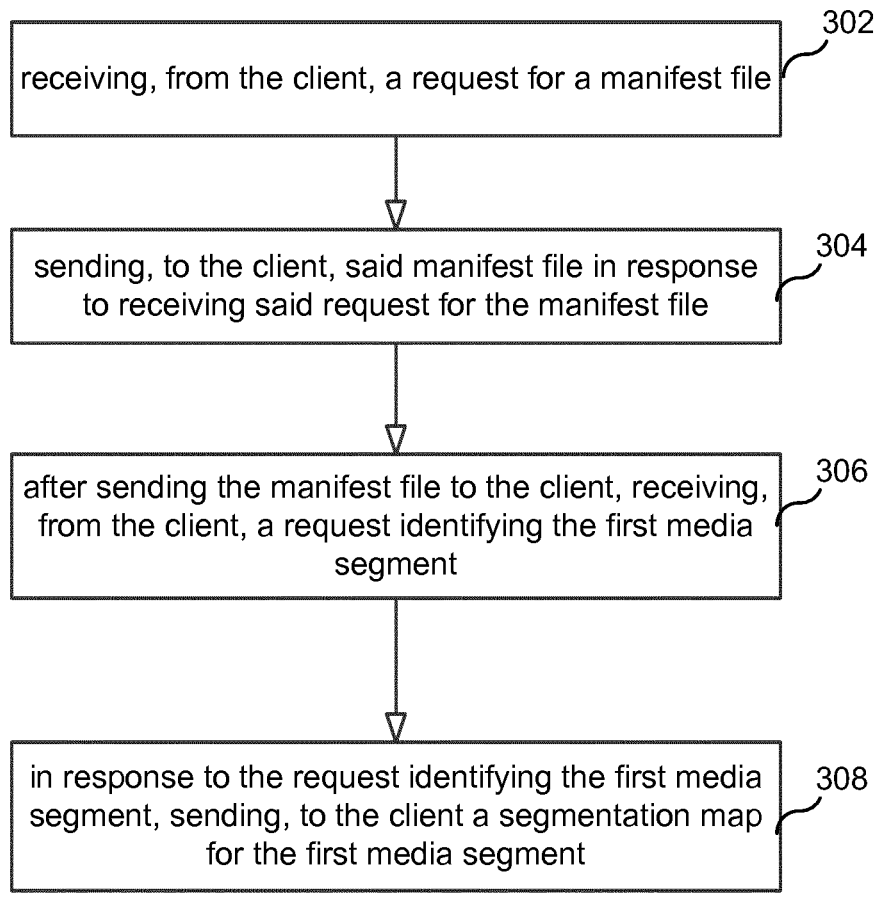
FIG. 3 illustrates a method according to an embodiment.

FIG. 3 illustrates exemplary embodiments for delivering (or receiving) a dynamically generated media stream. For example, in some embodiments, the dynamically generated media stream represents a live source of data, such as a live television feed. In some embodiments, the methods may take place over the Internet, using HTTP, and both client 102 and server 104 may be Internet-enabled devices. According to one embodiment, a method for delivering a dynamically generated media stream to a client, the media stream comprising a plurality of media segments including a first media segment and a second media segment, is provided. The method comprises receiving, from the client, a request for a manifest file (step 302). In some embodiments, the manifest file comprises information for enabling the client to generate requests for the media segments. The method further comprises sending, to the client, the manifest file in response to receiving the request for the manifest file (step 304). The method further comprises, after sending the manifest file to the client, receiving, from the client, a request identifying the first media segment (step 306). In some embodiments, the request identifying the first media segment was transmitted by the client as a result of the client processing the manifest file. In some embodiments, the request is transmitted by the client before the server is able to provide the complete media segment to the client (e.g., the server has not completed generating the moof and mdat boxes).

The method further comprises in response to the request identifying the first media segment, sending, to the client a segmentation map for the first media segment (step 308). In some embodiments, the first media segment comprises an ordered set of fragments including a first fragment (e.g., moof box) and a second fragment (e.g., mdat box) and the segmentation map comprises: first fragment metadata comprising a first fragment identifier for use in retrieving the first fragment from a server, second fragment metadata comprising a second fragment identifier for use in retrieving the second fragment from a server, and ordering information identifying the ordering of the fragments within the set of fragments, including information indicating that the first fragment is ordered before the second fragment.

Figure 4:
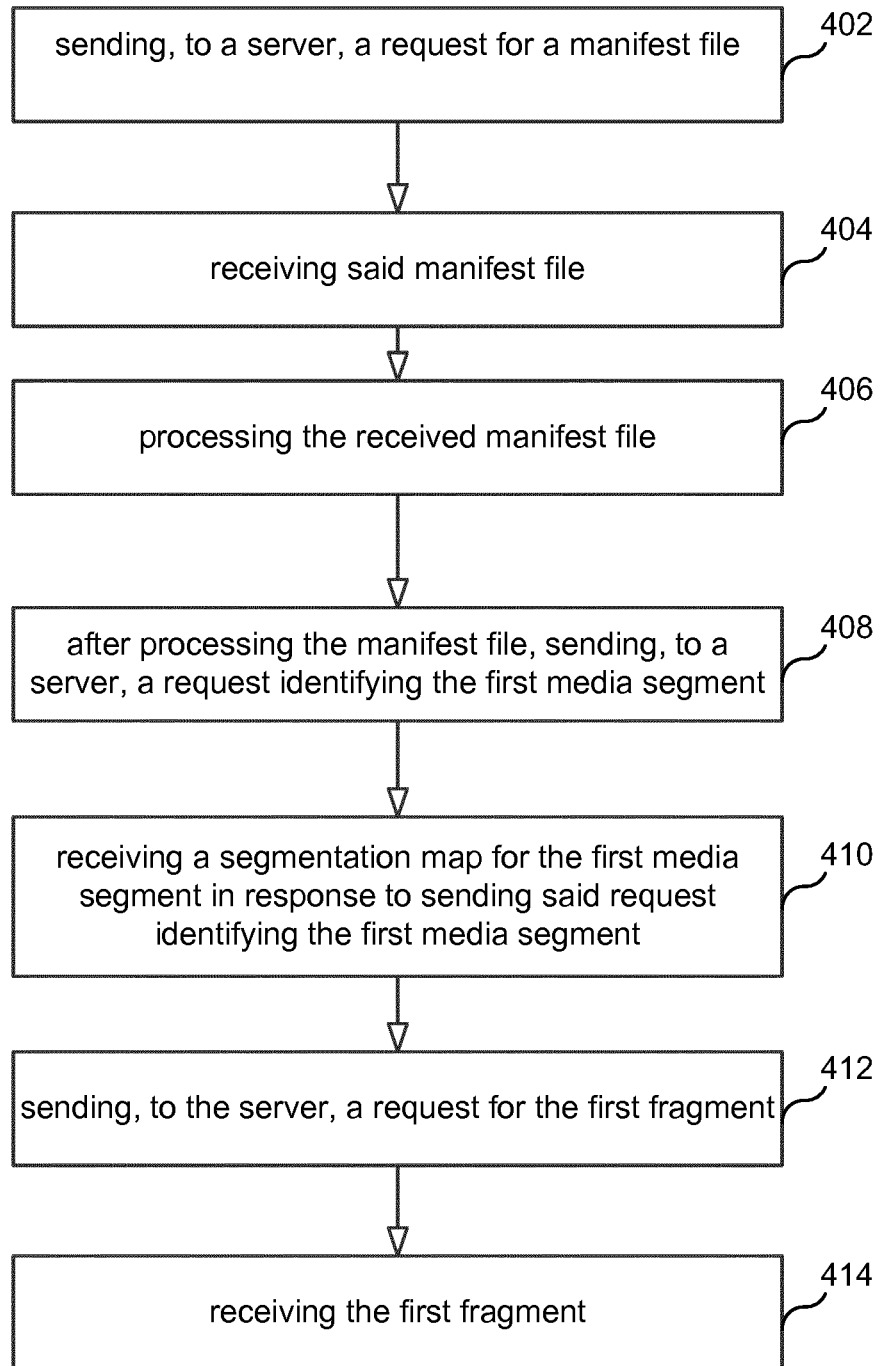
FIG. 4 illustrates a method according to an embodiment.

FIG. 4 illustrates exemplary embodiments for receiving a dynamically generated media stream, the media stream comprising a plurality of media segments including a first media segment and a second media segment is provided. The method comprises sending, to a server, a request for a manifest file (step 402). In some embodiments, the manifest file comprises information for enabling the client to generate requests for the media segments. The method further comprises receiving the manifest file (step 404). The method further comprises processing the received manifest file (step 406). The method further comprises after processing the manifest file, sending, to a server, a request identifying the first media segment (step 408). The method further comprises receiving a segmentation map for the first media segment in response to sending the request identifying the first media segment (step 410). In some embodiments, the first media segment comprises an ordered set of fragments including a first fragment and a second fragment and the segmentation map comprises: first fragment metadata comprising a first fragment identifier for use in retrieving the first fragment from a first server, second fragment metadata comprising a second fragment identifier for use in retrieving the second fragment from a server, and ordering information identifying the ordering of the fragments within the set of fragments, including information indicating that the first fragment is ordered before the second fragment. The method further comprises sending, to the server, a request for the first fragment (step 412). The method further comprises receiving the first fragment (step 414).

Figure 5:
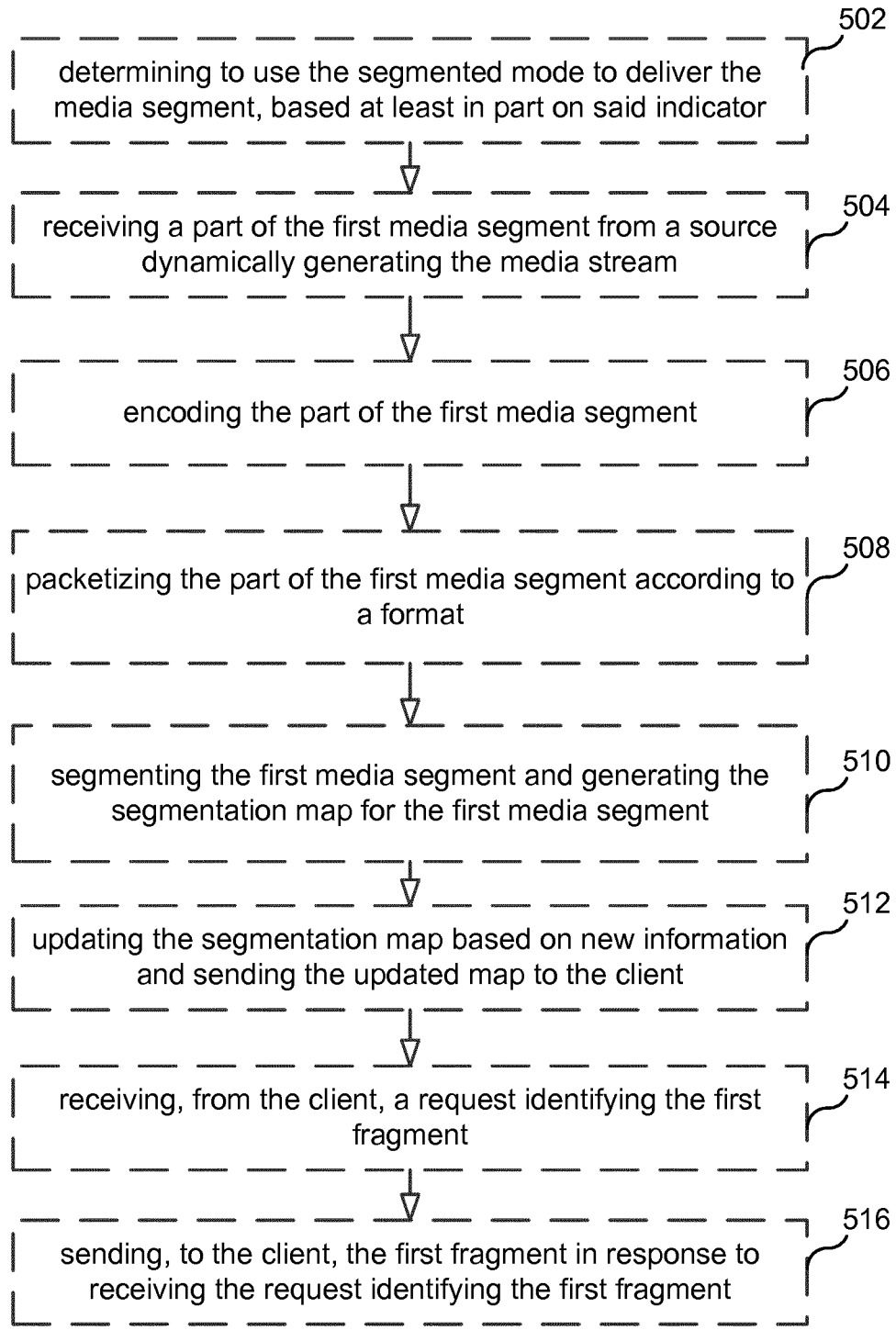
FIG. 5 illustrates a method according to an embodiment.

FIG. 5 illustrates additional exemplary embodiments for delivering a dynamically generated media stream. For example, in some embodiments, client 102 may include in the request for the first media segment (or any other request) an indicator that the client supports a segmented mode. In some embodiments, the method for delivering a dynamically generated media stream to a client further comprises determining to use the segmented mode to deliver the media segment, based at least in part on the indicator (step 502). For example, if the client does not support the segmented mode, server 104 may not use the segmented mode, and therefore will not send a segmentation map to the client. In some embodiments, the determination to use the segmented mode to deliver the media segment further depends on whether the first media segment has been fully generated. For example, if the first media segment has been fully generated, server 104 may use conventional file streaming techniques to deliver the first media segment. On the other hand, if the first media segment has not been fully generated, server 104 may determine to use segmented mode to deliver the first media segment.

Embodiments of the present invention support a number of ways to process or prepare media received from a source so that it is ready for delivery. For example, in some embodiments, the method may further comprise receiving a part of the first media segment from a source dynamically generating the media stream (step 504). In an embodiment, the part of the first media segment is received via source feed 302. In some embodiments, the part of the first media segment corresponds to at least one of a media sample and a media application data unit (ADU) (e.g., the part of the first media segment may contain media frames (i.e., audio frames and/or video frames). In some embodiments, the part of the first media segment that is received is encoded, for example in an audio or video format, such as H.264 or MPEG-4 Advanced Video Coding (AVC). In other embodiments, the method may further comprise encoding the first media segment (step 506). For example, the encoding may transform the part of the first media segment to an audio or video format, such as H.264 or MPEG-4 Advanced Video Coding (AVC). In an embodiment, encoder 304 performs this step. The method may further comprise packetizing the part of the first media segment according to a format (step 508). For example, the format may be the ISO Base Media File Format (ISOBMFF). In an embodiment, packetizer 306 performs this step. The method may further comprise segmenting the first media segment and generating the segmentation map for the first media segment (step 510). For example, the segmentation map may have one or more properties of the exemplary segmentation maps disclosed in this application. In an embodiment, segmenter 308 performs this step. In some embodiments, generating the segmentation map for the first media segment is based on the packetized part of the first media segment in the format.

In some embodiments, the method further comprises updating the segmentation map based on new information and sending the updated map to the client (step 512). For example, at the time of initially creating the segmentation map, certain information may not be known (such as length or position information of individual fragments within the media segment). Upon completing encoding and packetizing of the media segment, or of a particular fragment within the media segment, server 104 may update the segmentation map with new information (e.g., length or position information) at that time. The method may further comprise receiving, from the client, a request identifying the first fragment (step 514); and sending, to the client, the first fragment in response to receiving the request identifying the first fragment (e.g., the first fragment may be sent to the client using HTTP chunking) (step 516).

Figure 6:
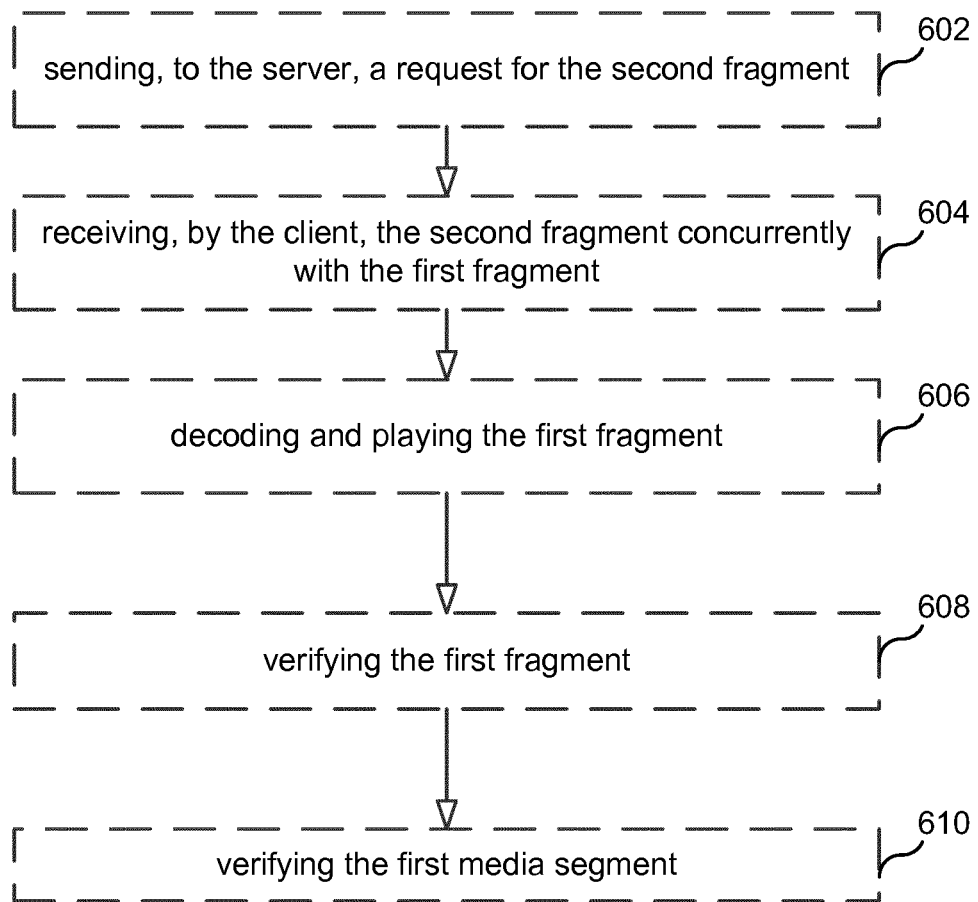
FIG. 6 illustrates a method according to an embodiment.

FIG. 6 illustrates additional exemplary embodiments for receiving a dynamically generated media stream. In some embodiments, the method for receiving a dynamically generated media stream may further comprise sending, to the server, a request for the second fragment (step 602). The method may further comprise receiving, by the client, the second fragment concurrently with the first fragment (step 604). In some embodiments, the client may continue sending requests for fragments, and receiving the corresponding fragments, until the client has received all of the fragments for the media segment. The method may further comprise decoding and playing the first fragment (step 606). In some embodiments, decoding and playing the first fragment occurs prior to the client receiving a third fragment of the first media segment. The method may further comprise verifying the first fragment (step 608). The method may further comprise verifying the first media segment (step 610). In some embodiments, decoding and playing the first fragment occurs after verifying the first fragment and before verifying the first media segment.

Embodiments of the present invention are applicable to a number of different delivery mechanisms. For example, in some embodiments the client may actively request, or pull, data from a server (including, for example, fragments of media segments). In other embodiments, the client may be passive, and some other entity may push data to the client (including, for example, fragments of media segments).

Figure 7:
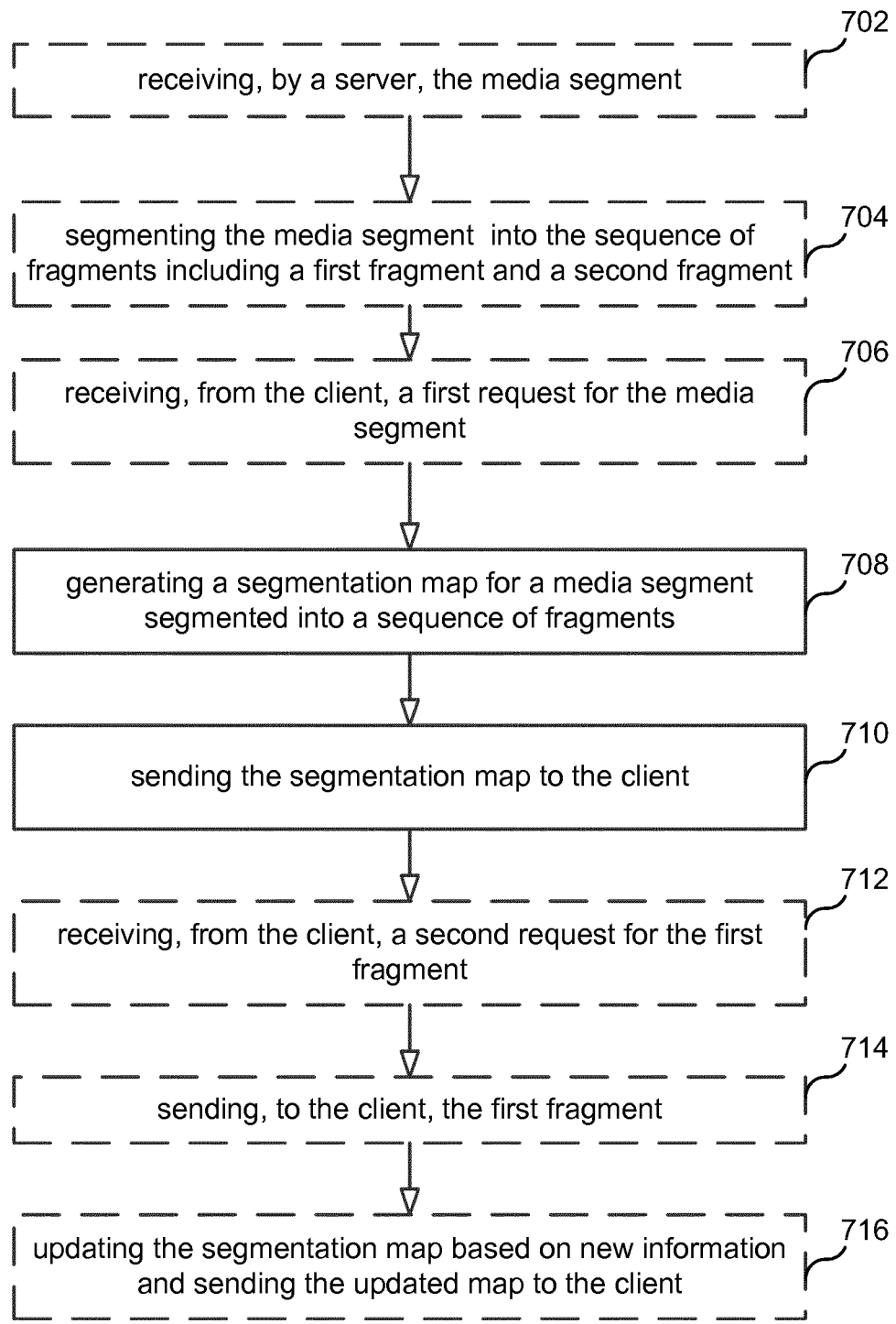
FIG. 7 illustrates a method according to an embodiment.

FIG. 7 illustrates exemplary embodiments for delivering a media stream. According to one embodiment, a method for delivering a media segment to a client is provided. The method comprises generating a segmentation map for a media segment segmented into a sequence of fragments (step 708). The method further comprises sending the segmentation map to the client (step 710). In some embodiments, the method may further comprise receiving, by a server, the media segment (step 702). For example, the server may receive the media segment via source feed 302, and pass the segment through one or more of encoder 304, packetizer 306, and segmenter 308. The method may further comprise segmenting the media segment into the sequence of fragments including a first fragment and a second fragment (step 704). For example, such segmenting may be done by segment 308. The method may further comprise receiving, from the client, a first request for the media segment (step 706). The method may further comprise receiving, from the client, a second request for the first fragment (step 712). The method may further comprise sending, to the client, the first fragment (step 714). The method may further comprise updating the segmentation map based on new information and sending the updated map to the client (step 716). For example, in some embodiments the new information includes one or more of a length of one of the plurality of fragments, a start position of that fragment in the media segment, and an end position of that fragment in the media segment. In some embodiments, one or both of updating the segmentation map and sending the updated map to the client may be performed in response to the client requesting an updated segmentation map. In some embodiments, the server may direct the client to request the fragment from a secondary server (e.g., an out-of-band server in a different trust domain). In some embodiments, the segmentation map will include information directing the client to a secondary server for a particular fragment.

Figure 8:
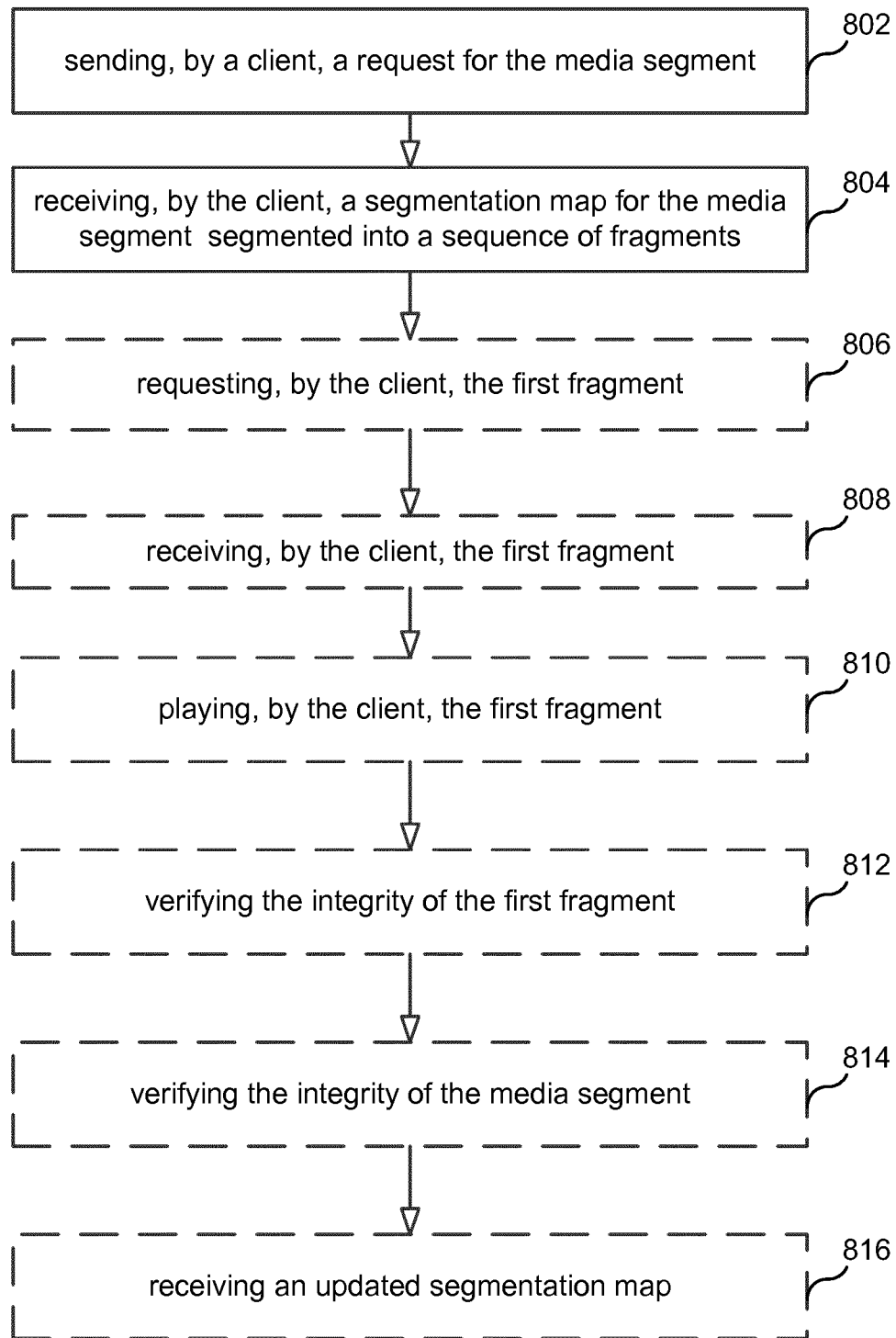
FIG. 8 illustrates a method according to an embodiment.

FIG. 8 illustrates a method, according to an exemplary embodiment, for decoding a media segment. The method comprises sending, by a client, a request for the media segment (step 802). The method further comprises receiving, by the client, a segmentation map for the media segment segmented into a sequence of fragments (step 804). In some embodiment, the method may further comprise requesting, by the client, the first fragment (step 806). The method may further comprise receiving, by the client, the first fragment (step 808). The method may further comprise playing, by the client, the first fragment (step 810). The method may further comprise verifying the integrity of the first fragment (step 812). The method may further comprise verifying the integrity of the media segment (step 814). The method may further comprise receiving an updated segmentation map (step 816). In some embodiments, for each of the other of the plurality of fragments, the method may further include requesting, receiving, and playing such fragment. In some embodiments, prior to playing any fragment of the media segment, the client first verifies the integrity of such fragment and only plays such fragment if the client positively verifies the integrity of such fragment. In some embodiments, the client may order the requests for fragments in a different order than the logical ordering corresponding to the sequence of fragments. In some embodiments, the order the requests for fragments are made in, depends at least in part on dependency information, such as size dependency and content dependency information regarding each of the fragments. In some embodiments, the client may make requests for different fragments in parallel. In some embodiments, the fragments may be received from different servers, and in some embodiments the requests for fragments may be sent to different servers.

Figure 9:
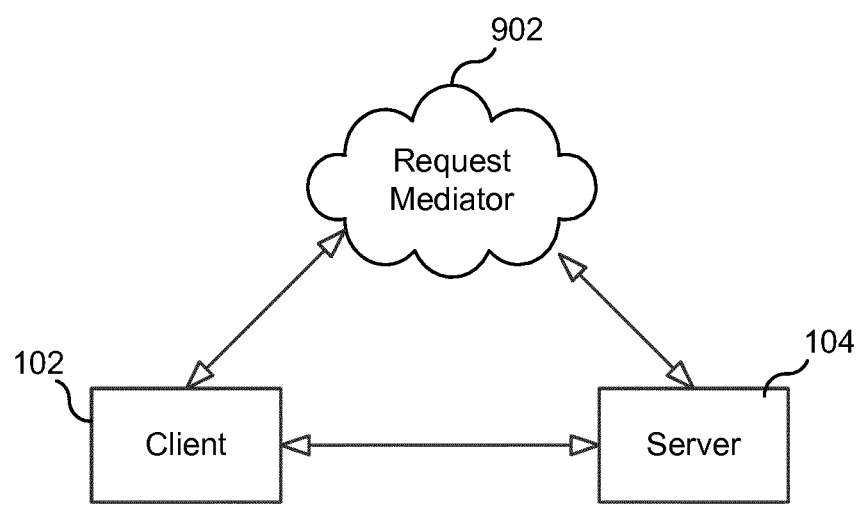
FIG. 9 illustrates a client-server interaction according to exemplary embodiments of the present invention.

Referring now to FIG. 9, client 102 may also communicate with a request mediator 902. Request mediator 902 may be part of client 102 (e.g., the client 102 may execute an app, such as a video player, that communicates with a request mediator component of client 102), or Request mediator 902 may be located near client 102, or it may be part of server 104, or located near server 104, or it may be separate and independent from either client 102 or server 104. After receiving a segmentation map from server 104, client 102 (e.g., the app) may send a series of requests for the various media fragments. The segmentation map may indicate that some fragments have dependency on others. This may mean, for example, that before one fragment may be retrieved, another fragment must be retrieved first. The role of request mediator 902 is to handle this dependency information. Thus, client 102 (e.g., the app) may send fragment requests to mediator 902, and mediator 902 may then forward the request to server 104 at the appropriate time based on the dependency information included in the segmentation map. That may mean, for example, that mediator 902 immediately forwards a request to server 104 (for example, if there is no dependency), or it may mean that mediator 902 causes a request to hang or block until a condition is satisfied (for example, any dependency is resolved). Request mediator 902 may also contain logic to allow it to mediate requests based on fragment priority, or other fragment metadata.

Figure 10:
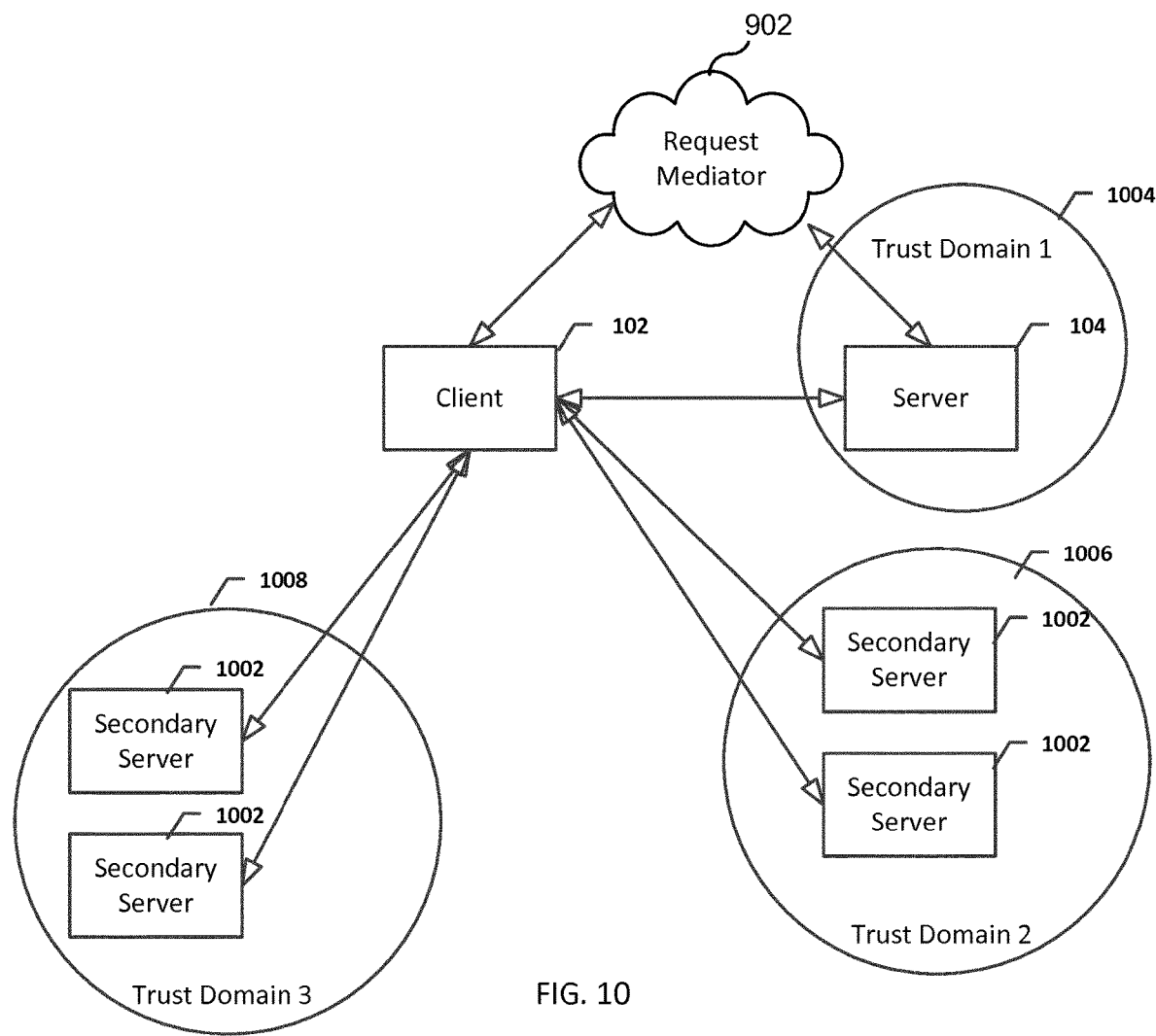
FIG. 10 illustrates a client-server interaction according to exemplary embodiments of the present invention.

Referring now to FIG. 10, client 102 may also communicate with a number of secondary servers 1002. Thus, rather than receiving all media fragments from server 104, client 102 may receive one or more fragments from one or more of the different secondary servers 1002. According to some embodiments, client 102 will initially request fragments from server 104, but the requests will then be redirected to one of the secondary servers 1002. According to some embodiments, client 102 will initially request fragments directly from one of the secondary servers 1002, for example, based on information contained in the segmentation map (e.g., the fragment locator may point to a secondary server). According to some embodiments, request mediator 902 will direct requests to one of the secondary servers. For example, request mediator 902 may act as a load balancer, and may make a decision to direct a request to a secondary server based on a number of factors such as volume of requests sent to other servers and available bandwidth, or based on geographical considerations.

It is possible that server 104, and one or more of the secondary servers 1002 reside in different trust domains (e.g., one of the three trust domains 1004, 1006, 1008 shown in FIG. 10). This may implicate the same origin policy, and has implications for a client who wishes to verify the integrity of a resource before accessing that resource. Embodiments of the present invention fully support this, and enable a client to verify integrity across a number of different trust domains, as explained more fully below.

Although not fully shown in the figure (for the sake of simplicity), in some embodiments each of client 102, server 104, request mediator 902, and secondary servers 1002 are each capable of communicating with each other (for example, server 104 may communicate with each of secondary severs 1002, and vice versa). Note also that the responsibilities of server 104 may be distributed among one or more secondary servers 1002. This means, for example, that the server that encodes the media resource, the server that generates the segmentation map, the server that mediates client requests, and the server or servers that serve media resource fragments to the client, may each be different servers.

Confidentiality and Integrity Solutions

The segmentation map provides advantages whether confidentiality and integrity mechanisms are employed or not. However, where such mechanisms are employed, the segmentation map provides additional advantages over the state of the art.

Typically, the integrity of the full resource can be determined in multiple ways. The most basic one is to verify the resource when it has been fully received in the client. The most basic of such solutions is to simply calculate a hash value over the full resource and include that in the segmentation map assuming secured delivery from the authoritative domain for the resource. Several solutions exist for this, such as Content-Signature Header Field for HTTP (see, e.g., [CONTENTSIG]) or Merkle Integrity Content Encoding (see, e.g., [MICE]). However, there is a clear downside to using these approaches for segmentation of a resource that a client may want to consume progressively. The client or application must, for such approaches, wait until the full resource has been delivered if wants to avoid using non-verified data. Of course, if using non-verified data were acceptable, an alternative would be to consume data and then warn the user or otherwise handle if the resource later fails verification. This approach can be risky, and unadvisable, as it depends on using unverified and therefore untrusted data.

Another problem with such approaches for verification is that if the full resource verification indicates that the resource does not verify correctly, then the client cannot determine which fragment caused the verification to fail. To resolve this issue, individual resource fragments need their own integrity verification information. This can be accomplished by treating each fragment as its own resource on a delivery-protocol level, and having the segmentation map indicate the integrity verification mechanism used for each fragment, along with any parameters associated with the integrity verification mechanism.

To enable verification when progressively consuming the resource fragment, the integrity solution needs to be provided over suitable chunks of the resource fragment as they are delivered. Such a solution should preferably be flexible regarding record sizes to avoid blocking issues when the amount of data provided in each chunk doesn't align with fixed record sizes. For media streams like video, a single media sample (e.g., an encoded video frame) is a suitable chunk to protect. MICE could be usable for data that is prepared and where full DASH segments are available prior to starting delivery of the resource segment (i.e., where the media stream is not dynamically generated). The fixed record size (imposed by MICE) can in that setting be worked around by delivering full records in each delivery chunk.

However, for live or dynamically-generated content, where the next media sample is not available at the time of preparing for transmission of a particular chunk, the above approach does not work well. Instead, another approach is to hash the individual chunks (instead of the full media segment) and include the resulting hash with each record. Both a signature over the hash, or using a keyed hash, may be used to make the hash verifiable in the client as originating from a source trusted by the provider of the segmentation map. This solution avoids adding any significant delay due the integrity mechanism and its structure for protecting data.

Data integrity (is that data trustworthy) is one important aspect of security. Another aspect is confidentiality (keeping the data hidden from non-authorized parties).

Embodiments of the present invention allow for delivery of a resource to be spread out over multiple entities (e.g., edge servers or caches close to a user). But having multiple entities that can potentially produce and deliver different fragments of a given media resource presents some complications regarding confidentiality. For security reasons, the different entities may not share a security context. Thus, the segmentation map may need to indicate resource-fragment-specific security-context information, such as keys.

Another aspect of confidentiality for resource fragments that are progressively consumed is to ensure that a fragment can both be decrypted from its starting point, and the data on chunk-level can be decrypted. This may in some cases require encryption-layer padding to ensure that the encryption algorithm can perform decryption at the chunk boundary.

Utilizing Different Trust Domains

By utilizing general locators for the individual resource fragments, a particular resource fragment can potentially be retrieved from any location. That is, the retrieval point of one fragment may not depend on the retrieval point of another fragment. Thus, different fragments may be retrieved from different trust domains (e.g., different hosts, perhaps having different domain name system (DNS) names). The resource segment could also be provided using the OOB content-encoding, enabling the main domain for the resource fragment in its turn to point at one or multiple secondary resources where the content for the fragment can be retrieved.

These two solutions can potentially be integrated into a combined segmentation map with multiple OOB secondary resources, or the two solutions can be applied after each other in suitable combinations.

The possibility that is created both by the segmentation map as well as the OOB encoding solution to point at any resource location has various implications. For example, in HTTP, this may affect the same origin policy (see, e.g., [RFC6454]), enabling loading of resources outside of the control of the domain of the full resource (main domain). To avoid this outcome, appropriate security models may be applied. One possibility is that the main domain (i.e., that provides the segmentation map) provides a way to verify the integrity of the retrieved segment from the secondary domain, i.e., that what is retrieved from the secondary domain matches what is intended according to the main domain. This is most easily realized by including a hash for the fragment in the segmentation map. Another possibility (based on the main domain trusting the secondary domain) is to have some way for the main domain to indicate the trust the main domain has in the secondary domain. For example, the main domain may do so by indicating in the segmentation map which key or certificate the secondary domain will use to prove the integrity of the resource fragment.

Example Embodiment of the Segmentation Map

There are many different forms and formats for a segmentation map that fulfills most or all of the above-described characteristics. One possible embodiment of the segmentation map, which may be used with HTTP 1.1, is provided below.

In this example a client requests a resource (which in this example is a fragmented MPEG-4 (mp4) media segment) at the locator (e.g., URL) "https://example.org/xyz/seg-2-14.mp4" using HTTP 1.1. The client indicates that it supports a content encoding called "segmented" to indicate its support for the segmentation mechanism. The server also supports and utilizes the segmentation mechanism in the response. The response includes an indication of the usage of the segmented content encoding, and the body includes a JSON encoded segmentation map describing the fragments. In this case, the first request arrives prior to the full resource having been constructed.

The HTTP Request is as follows:
GET /xyz/seg-2-14.mp4 HTTP/1.1
Host: example.org
Accept-Encoding: gzip, segmented
HTTP/1.1 200 OK
Date: Thu, 24 Oct. 2016 16:54:00 GMT
Content-Type: application/json
Cache-Control: max-age=10, public
Expires: Thu, 24 Oct. 2016 16:54:03 GMT
Content-Encoding: segmented
Content-Length: XYZ
Vary: Accept-Encoding The Response to the HTTP Request, including the exemplary segmentation map, is as follows:

```
"Resource": "https://example.org/xyz/seg-2-14.mp4",
"Content-Type": "video/mp4"
"Crypto-Key": {keyid="a1"; aesgcm="csPJEXBYA5U-Tal9EdJi-w"}
"Update-Hint": {"Content-Dependency":{[4]}, "Expires":" Thu, 24 October 2016 16:54:03 GMT"}
"Fragments": {
[
    {
        "Fragment":"1",
        "FL": "https://example.org/xyz/seg-2-14.mp4.frag1",
"https://backup.example.org/xyz/seg-2-14.mp4.frag1"
        "Offset":"0-493/494",
        "Size-Dependency": { },
        "Content-Dependency": { },
        "Priority": "3",
        "attributes":
            {
                "Content-Encoding": "aesgcm"
                "Encryption": {keyid="a1";
salt="Lb50cXdEZbMApPzVAzAXBO"}
            }
    },
    {
        "Fragment":2,
        "FL": "https://example.org/xyz/seg-2-14.mp4.frag2",
"https://backup.example.org/xyz/seg-2-14.mp4.frag2"
        "Offset":"494-/",
        "Size-Dependency":{ },
        "Content-Dependency":{ },
        "Priority": "1",
        "attributes":
        {
            "Content-Encoding": "aesgcm",
            "Transfer-Encoding":"chunked",
            "Encryption": {keyid="a1";
salt="mGlyNgksqELbSqrAB09Lsg"},
            "Type-Specific": "moof"
        }
    },
    {
        "Fragment":"3",
        "FL": "https://example.org/xyz/seg-2-14.mp4.frag3",
"https://backup.example.org/xyz/seg-2-14.mp4.frag3"
        "Offset":"-/12",
        "Size-Dependency": {["1", "2"]}
        "Content-Dependency": {["4"]},
        "Priority": "1",
        "attributes":
        {
            "Content-Encoding": "aesgcm"
            "Encryption": {keyid="a1"; salt="3hVJ0GeuOz1epckD3IsIOa"}
        }
    },
```

```
{
    "Fragment":"4",
    "FL": "https://example.org/xyz/seg-2-14.mp4.frag4",
"https://backup.example.org/xyz/seg-2-14.mp4.frag4"
    "Offset":"-/",
    "Size-Dependency": {["3"]}
    "Content-Dependency":{ },
    "Priority": "1",
    "attributes":
    {
        "Content-Encoding": "aesgcm",
        "Transfer-Encoding":"chunked",
        "Encryption": {keyid="a1"; salt="hynhpnHujSQBb64swbQglf"},
        "Type-Specific": "mdat-samples"
    }
  }
]}
```

The segmentation map starts with resource level properties. This includes the actual media type of the resource described by the segmentation map ("Content-Type"). This is also the place where one can include resource level integrity mechanisms, like a hash over the full resource. However, that is not possible in this example, as the resource is not yet fully constructed. However, the crypto key used for encrypting the different resource fragments is included in the "Crypto-Key" parameter. The full resource URL is included just to enable to handle the segmentation map outside of the context of the HTTP request.

The segmentation map also includes an "Update-Hint" attribute. This indicates when it is recommended to update the segmentation map for more complete information. In this case, there is a Content-Dependency attribute, which has the meaning that the update is dependent on the content availability of fragment identified as "4". As will be described later, this indicates that when the resource content is known on the server side, then this segmentation map can be constructed without open ranges (i.e., with known values for the start and end positions). However, the Content-Dependency attribute requires one to request the data to determine when the segmentation map could be updated. As this approach requires a fragment to be processed before requesting an updated map, another complementary approach is to use a more time based hint. This example includes the HTTP Expires header, to indicate that 3 seconds after the server generated the segmentation map, the segmentation map should be updated. In this case, 3 seconds is indicated based on knowledge that by this time the full resource will have been constructed. The Expires header is also included as a parameter in the "Update-Hint" attribute.

After the resource level attribute, an array describing the ordered sequence of the fragments follows. In this example, the resource (media segment) is logically segmented into four fragments: a first fragment corresponding to the styp box of the media segment; a second fragment corresponding to the moof box of the media segment; a third fragment corresponding to the header portion of the mdat box; and a fourth fragment corresponding to the payload portion of the mdat box (i.e., the media samples).

A note on terminology: the segmentation map does not include "fragments" in the sense of including the actual resource data; instead, the segmentation map includes metadata associated with each resource fragment, including information about how to obtain the actual resource data. Thus, when describing "the first fragment" in the segmentation map, what is meant is the first fragment's metadata, or the information associated with the first fragment that is stored in the segmentation map.

The first fragment in the array (that is, the first fragment's metadata) is now described. The first metadata information in the first fragment is an identifier for the fragment, given in the "Fragment" parameter and having a value of "1". This is followed by the "FL" parameter providing a set of fragment locations for this fragment, i.e., one or more URLs for where the fragment can be requested as its own resource. The "Offset" parameter provides the fragment's offset into (or position in) the full resource, and the length of the fragment, if known. The format is "start-end/length." Any of the three values part of the offset parameter, i.e., start position, end position, or length can be unknown (and thus not provided). This first fragment is at the start of the full resource (start=0) and has known length (length=494). In the example, the values "0-493/494" provide the start byte, end byte, and the length in bytes.

The next parameters for the first fragment are "Size-Dependency" and "Content-Dependency". These parameters can express what dependencies that exist on other fragments, by listing the fragments' identifiers. The size dependency parameter is a set of fragment identifiers, identifying what other fragments' size information (start and end positions, length) a client needs in order to determine the given fragment's start position. The content dependency parameter is a set of fragment identifiers, identifying what other fragments a client needs in order to receive the given fragment. In this case, both these dependency parameters comprise an empty set. The parameters, therefore, could be excluded in the HTTP Response, but are included here for sake of explanation. The priority parameter indicates the relative priority in requesting this fragment in relation to other fragments; in this example, a lower number is more important, or of greater priority. Potential usages of this information is described more below.

Still considering the first fragment's metadata, after the priority parameter, there follows a set of attributes which are related to the fragment as its own resource. That is, the parameters can be used when acquiring the fragment. In this case, the content encoding of "aesgcm" is indicated. AES GCM (see, e.g., [aesgcm]) is an encryption and integrity protection mechanism across the whole fragment. Fragments employing this content encoding can be decrypted continuously on a crypto-block basis from fragment start to end, but the integrity verification can only be performed when the full fragment has been delivered. This mechanism is keyed and salted; the key is the way to unlock the confidentiality protection, and also the way to be certain that the integrity was preserved for the fragment. In the present example, the actual key-id is common across all the resource fragments (and is the same as the resource-level key-id value included in the Crypto-Key parameter). However, each fragment in this example has an individual salted value in order to prevent using the same cipher on two fragments. This is provided by the "Encryption" parameter. This concludes the first fragment's metadata.

The second fragment is similar, but some differences in its parameters and additional parameters will be described. First, the fragments id is "2", and the URLs for this fragment are also pointing to the second fragment (that is, the URLs are different than those for the first fragment). The fragment's offset is providing a start position, but has unknown length and thus an unknown end position. The priority is set to 1, the most prioritized fragment in this full resource. The attributes include "Transfer-Encoding":"chunked". This indicates that this fragment can be delivered using the HTTP chunking mechanism. This can, for example, be used to deliver data progressively for the fragment as they are generated on the sever side (for example, as the media samples and their metadata are generated). The "Type-Specific": "moof" parameter and data are to be interpreted in the context of the full resource media type "video/mp4". For example, "moof" could indicate that this fragment is containing the moof box.

The third fragment (id="3"), in this example, has a known length (length=12 bytes) but as it is coming after the second fragment which has unknown length (until a client completely constructs the second fragment, or receives an updated segmentation map), the start or end offset are unknown. This fragment's dependency on other fragments are expressed using "Size-Dependency": {["1", "2"]} and "Content-Dependency": {["4"]}. The size dependency here means that the size and location of this fragment is given (that is, will be known by the client) when the size of fragments 1 and 2 are known. The Content-Dependency here indicates that the content of this fragment has a dependency on what is in fragment 4. In this case, this is because the fragment 3 represents a header that contains the length field for the data that is in fragment 4. So fragment 3 cannot be retrieved until fragment 4 has been completely generated, because fragment 3 cannot itself be generated until that time. As indicated, this fragment has a top priority, that is, priority 1.

The fourth fragment (id="4") has similar properties to the second fragment. However, due to the earlier fragments having an unknown size, the actual offset of this fragment is unknown at the time of generating the segmentation map. The priority of this fragment is "1", and it has no content dependency on the other fragments. However, its size and offset is dependent of fragment 3. The content-type specific hint "Type-Specific": "mdat-samples" indicates that this fragment starts at the start of the samples of the mdat box. This hint enables a media-type aware client to start consuming the data as it is being delivered by the chunked HTTP transfer.

As indicated above, in this example, each fragment's metadata includes a fragment identifier that indicates its order in a sequence (i.e., identifiers 1, 2, 3, and 4). Additionally, the fragments (i.e., the plurality of fragment metadata) are stored in an array, in this example, which is an ordered data structure, the array could impose an order on the fragments. In this example, both orders (the one implied by the data structure, and the one indicated by the fragment identifiers) are consistent.

Given the above-described segmentation map, a client can determine a suitable order for requesting the fragments. For example, for a client that has no storage restrictions and no issues with additional copies (e.g., client is willing to perform intermediate retrieval of fragments and then assembly of fragments), then one possible retrieval strategy would be to request fragment 2 (which has no content dependency and priority 1), and to request, in parallel, fragment 4 (also no dependency and priority 1), and request, in parallel, fragment 1 (also no dependency, but has a lower priority 3). That leaves fragment 3. Fragment 3 has a content dependency (on fragment 4), but in order to keep the delay minimal the client may make another parallel request for this fragment early, expecting that this request will hang until fragment 4 has been fully generated.

Figure 11:
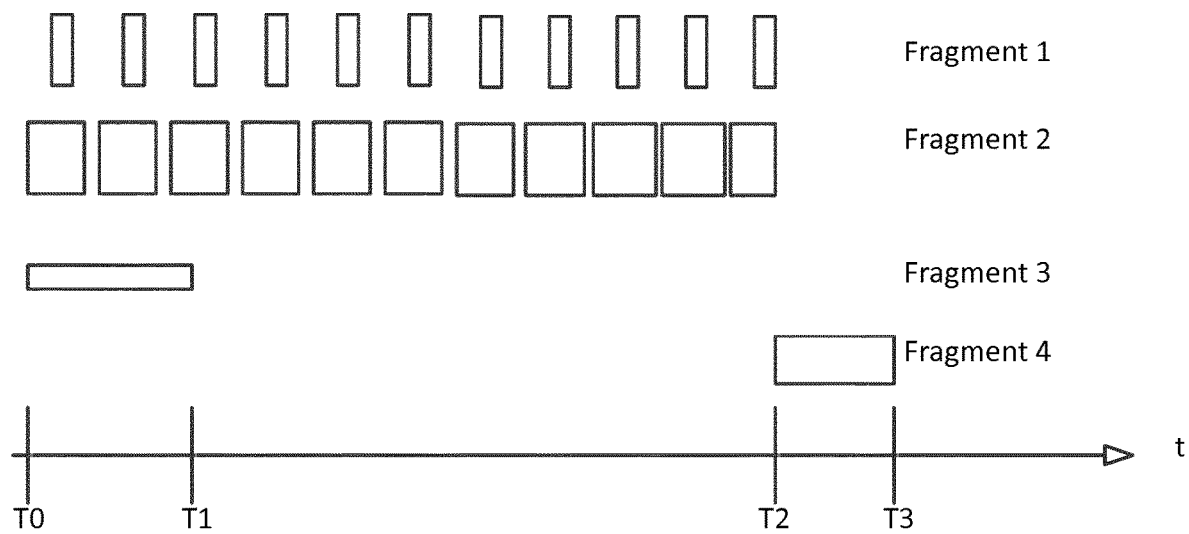
FIG. 11 illustrates an exemplary sequence according to exemplary embodiments of the present invention.

Referring now to FIG. 11, a possible scenario for the completion of the above requests is depicted. At the time of T0, the segmentation map has been processed by the client, and the client makes the requests as described above. The delivery of the fragments 1, 2, and 4 (each having no content dependency) begins as soon as the individual requests have been processed by the appropriate server. Even though fragment 1 has a lower priority, in this example it will complete first (at time T1) due to its limited size. Fragments 2 and 4 (per their Transfer-Encoding value) are using chunked delivery. In this case, chunks of metadata and media samples will be periodically transported as depicted by the bars. At time T2, the server (or servers) have completed the generation of data for fragments 2 and 4, and slightly after T2 their delivery will be complete and the chunked transport mechanism will indicate the completion of their delivery. The request for Fragment 3, according to this example, has been hanging since T0 up until T2, owing to its content dependency. At time T2, the data for fragment 3 (which is this example is length information identifying the length of the mdat box) has been generated and its delivery can start. The delivery of fragment 3 is completed at time T3. At time T3, the client can assemble the fragments into an ISO BMFF media segment.

As indicated above, the order of requests corresponds to a client that has no storage restrictions and no issues with additional copies. However, for a constrained receiver, for example a receiver that wants to avoid copies and minimize storage requirements, the receiver could use the size dependency metadata to determine in which order it can request fragments so that their position is known. In this case, the client would only request fragments 1 and 2 initially. This is because fragments 1 and 2 have no size dependency; that is, fragment 1 has a known size and starts at the beginning of the resource file. Fragment 2 starts directly after fragment 1, but its length is not initially known. Thus, the receiver will be able to write the data as it is received into a common continuously file. When Fragment 2 has been delivered, then fragments 3 and 4 would have known sizes. Thus, the client can then request both fragments 3 and 4 in parallel. With the known sizes and offset into the continuous file, the data can be written into the correct position directly on reception.

Another Example Embodiment used for DASH Live media segment

Embodiments of the segmentation solution described in this application can be used to reduce the delay from content ingestion start at a media delivery server until playout has started at the client ($T_{source\_to\_playback}$). Initially, the encoder generates encoded media content, either on an individual-frame level or on some slightly coarser level, such as for every group-of-pictures (GOP), in a format suitable for streaming delivery (e.g., H.264). From here, the encoded media is packetized, or passed through a packetizer or file format constructor, to put the encoded media in a format for delivery over a packet-based protocol such as HTTP (e.g., the encoded media is put into mp4 or ISOBMFF format).

An example will now be described, using DASH Live media streaming with ISOBMFF files.

For each media segment in this example, suppose that the segment has a length of 3 seconds and is provided in an ISOBMFF format. The file constructor creates the initial structure, in this case starting with a Segment Type Box (styp). This can be constructed based on the brand of the media segment and the file type used in the media initialization segment. For ISOBMFF files that are segmented according to DASH, an individual segment will use a movie fragment (moof) box to provide information about the location of the samples. The issue here is that some of the information in the moof box is dependent on the individual samples. One example of such a dependency is the Track Fragment Run Box (trun), which is part of the Track Fragment Box (traf), which is part of the moof box. The trun contains, for each sample stored inside the mdat, an offset to where this sample is located. Thus, the offset can only be written into the samples entry in the trun after the corresponding sample has been added into the mdat (i.e., when the offset is first known). As another example of a dependency, the boxes' length fields can be an issue, as the full length of a given box is not known until all boxes or samples are written into that box. If the box runs until the end of the file, it is possible to specify a value of 0 for length, which means the length of the box lasts until the end of the file. However, as the mdat box usually must follow the moof, the moof s length cannot typically be specified as 0.

Embodiments of the resource segmentation disclosed in this application may be applied to a media segment formatted according to the DASH specification's usage of the ISOBMFF. Doing so can reduce delay and enable HTTP chunked delivery or other push delivery as media sample data becomes available.

Figure 12:
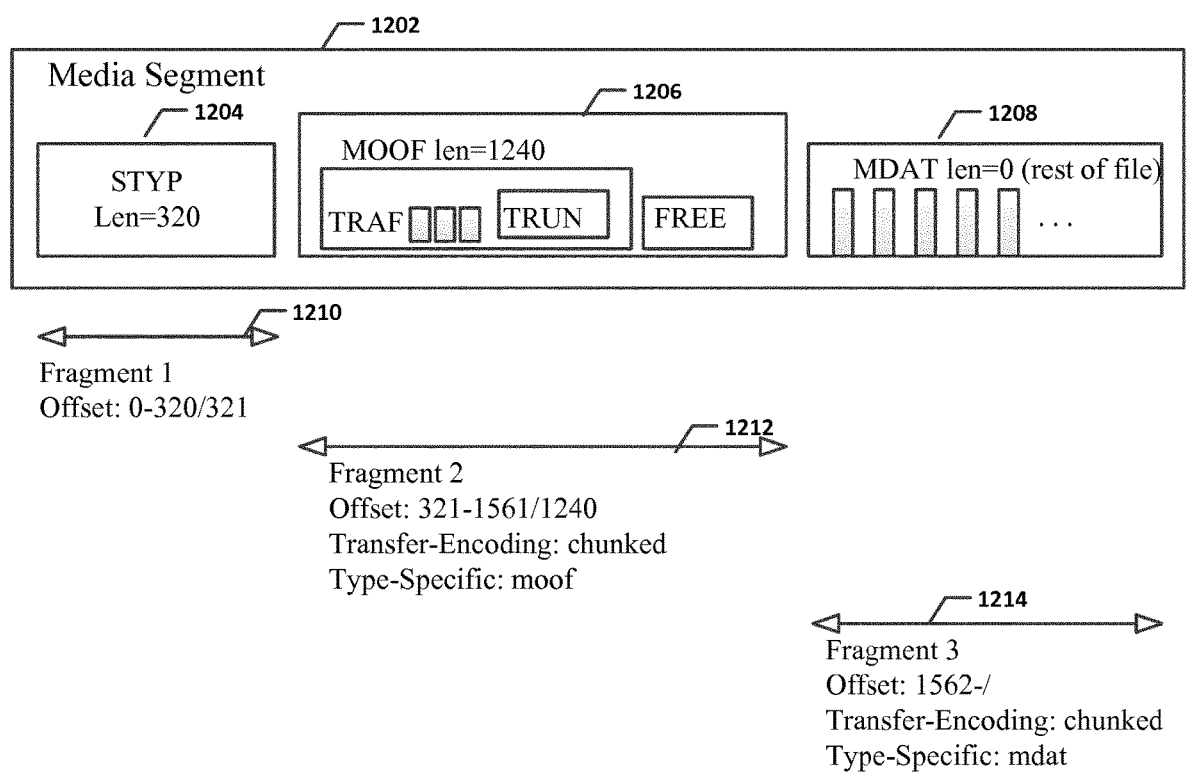
FIG. 12 illustrates an exemplary fragmentation of an ISOBMFF media segment according to exemplary embodiments of the present invention.

Referring now to FIG. 12, segmentation of the DASH media segment resource may proceed as follows. A first resource fragment 1210 may contain the start of the file, with information that can be generated initially. This fragment 1210 contains all the initial boxes 1204 that are known before all samples have been generated. The next resource fragment 1212 may contain the moof box 1206. As described in [S4-141201], it is possible to estimate, prior to all samples being generated, how much room space the moof box 1206 (along with the boxes contained within the moof box) will take. Such an estimate may include some reserve space. Thus, the full length can be estimated, and if there is any remaining space after the necessary samples have been added, this space can be marked as free using the free box (the free box is needed in this case to comply with the ISOBMFF specification). It is noted that underestimating the size here will result in a poorly or incompletely formatted segment; overestimating the size will result in wasted space. It is thus preferable to overestimate. An estimate may be based on, for example, a known or estimated frame rate and duration, leading to a known or estimated number of samples. The third resource fragment 1214 may contain the mdat box 1208. The size of this box 1208 is unknown prior to generating all samples, however the box will run until the end of the file. Thus, a length field value of 0 is possible to use. The third resource fragment 1214 mostly comprises the data part of the mdat box 1208, i.e., the data for the media samples. Here, the initial offset of the resource segment is known (fragment 3 offset=1562), but the offset corresponding to the end of the box is not known. Thus, the end offset is indicated as open ended.

The client can now start with first retrieving the first resource fragment. After that, the client may retrieve the second fragment (with the content of the trun boxes) and the third fragment (with the content of the mdat boxes); these two fragments can begin to be delivered using two independent HTTP resource requests with HTTP chunking for the individual resource fragments. The HTTP chunking is used to deliver appropriate chunks of data, for example, individual media samples, as they finish encoding, and the corresponding sample runs in the trun box as they are finished. When all the samples belonging to the media segment have been written into the mdat box, then the fragment is closed by using HTTP chunking to indicate the end of the chunked delivery. The moof fragment is also completed by writing the last part of the trun box, and the remaining space if any is consumed by the free box (thereby bringing up the byte count of the fragment to the predetermined length). This completes the delivery of the media segment.

The segment map can also contain hints if necessary to indicate to the receiving client what the start of the resource fragment is. For example, the segmentation map might indicate that one fragment is start of the mdat box (here, fragment 3), which would enable the client to consume the media samples as they get delivered by the http chunking.

The above examples use estimated and pre-assigned space for the resource segment where the content of the moof box is to be written, and especially the trun boxes. An alternative embodiment to not estimate how much space this box needs, and instead indicate that resource segment being of unknown length at the start and then to use the HTTP chunking to indicate when the full resource segment has been delivered, i.e., when all the samples intended to be included in the ISOBMFF segment file have been included, and the final position of all the data is known. When that happens, then the final trun is written and when the end of the moof box is determined, the HTTP chunking delivers an empty chunk to indicate that this is the end. However, to correctly indicate the length of the moof box in this case, the start of the moof box (including the length field) needs to be put into a separate fragment, so that this separate fragment can be delivered after the length of the moof box has been determined.

This approach (i.e., not estimate how much space the moof box needs) has the advantage of avoiding the risk for wrongly estimating the needed space, and also avoids wasting any unused space. However, if the final resource is to be stored for future usage, then additional copying operations will normally be required to assemble the resource fragments as one continuous byte stream for the final assembled resource. But, in some use cases this is not the prime usage, and instead the earliest possible access to the data, while still formatted as following the live profile of the ISOBMFF is the primary usage.

Comparative Example

A comparative example is now provided. A server (such as server 104) is serving two clients, the first, a client that is able to receive and process a segmentation map according to presently disclosed embodiments (such as client 102) (called a "smart client"), the second, a conventional client that is not able to receive and process a segmentation map according to presently disclosed embodiments (called a "dumb client" or "conventional client").

The server is providing access to a live streaming media event (e.g., an evening TV news program). The server is continuously receiving the source feed, as the event is ongoing. The server may know very little about the source feed, such as the total duration, quality of source feed, expected viewership, and so forth; alternately, such information may be fully determined beforehand, or the server may have some information about which to form an estimate of such things (e.g., typical start and stop time of the program, and typical quality of incoming feed). At any event, the server prepares a manifest file for the live streaming media event. This file will break up the event into a number of segments, or media resources, typically individually between 2 seconds and 10 seconds in duration. The manifest file may contain hints about when the client should access particular segments, or media resources. For example, the server may know or estimate that it will begin to receive a first resource at time t0 and that it will take A seconds to process the resource (e.g., to encode and packetize the resource so that it is ready for delivery to a client).

The conventional client will follow the manifest file, because it is not able to begin to receive an individual media resource until the server has processed it, and prepared it for delivery. Therefore, the conventional client will request the first media resource at or after time t1 (t1=t0+A). Thus, the delay $T_{source\_to\_reception}$ for the conventional client is A. Typical values of A may be between 2 seconds and 10 seconds.

Further, the conventional client will have to receive and process the entire resource before beginning playback, which will take B seconds. Thus, the conventional client cannot begin playback until time t2 (t2=t1+B=t0+A+B), and so the delay $T_{source\_to\_reception}$ for the conventional client is B. This results in a delay $T_{source\_to\_playback}$=A+B.

On the other hand, the smart client, that is the client that is able to receive and process a segmentation map, will be able to request the first media resource prior to the server fully processing it. It may only take the server C seconds to generate the segmentation map, and begin to provide parts of the media resource to the client. Thus, the smart client will request the first media resource at or after time t1' (t1'=t0+C). Thus, the delay $T_{source\_to\_reception}$ for the smart client is C. Typical values of C may be about 200 ms. This time consists of time to form the segmentation map, an extra round trip to deliver the segmentation map and then have the client ask for the fragment and then be able to start delivering the fragment.

Further, the smart client is able to begin playback prior to receiving the entire segment. For example, as described above, an application-level hint may enable the client to do so, for example within D seconds of reception. Thus, the smart client may begin playback at t2' (t2'=t1'+C=t0+C+D), and so the delay $T_{source\_to\_reception}$ for the smart client is D. This results in a delay $T_{source\_to\_playback}$=C+D. In the present example, because the MOOF is relatively small (a few kb), the difference B–D is, in this example, on the order of a few milliseconds.

According to this example, the delay $T_{source\_to\_reception}$ may be reduced from about 2-10 seconds to about 200 milliseconds, or about 90%-98%. The delay $T_{reception\_to\_playback}$ may be reduced by a few milliseconds. Overall, this results in a significant reduction in delay from source ingestion to playback.

As is apparent from this example, the time when a resource segment is available for consumption by a client will differ significantly depending on whether the client supports the segmented mode. In some embodiments, a smart client that supports the segmented mode may determine to ignore or appropriately modify the availability hints provided in a manifest file. In some embodiments, a server may provide one manifest file to a conventional client, and a different manifest file (having revised availability hints) to a smart client.

Figure 13:
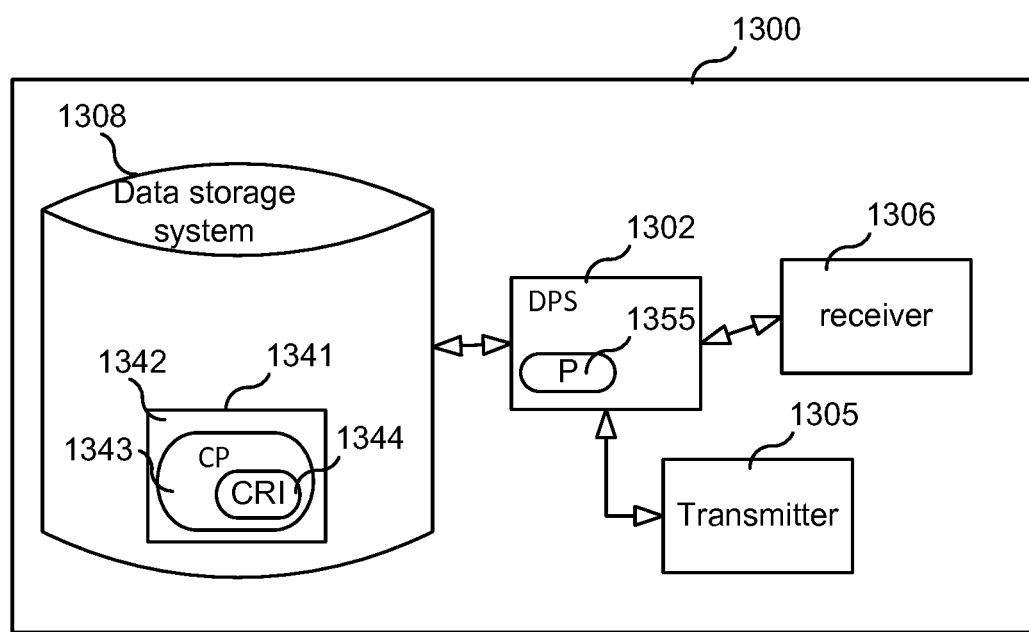
FIG. 13 illustrates a block diagram of an apparatus according to some embodiments.

FIG. 13 is a block diagram of an apparatus 1300, according to some embodiments, that may be used to implement either client 102 or server 104. As shown in FIG. 13, the apparatus may comprise: a data processing system (DPS) 1302, which may include one or more processors 1355 (e.g., a general purpose microprocessor and/or one or more other processors, such as an application specific integrated circuit (ASIC), field-programmable gate arrays (FPGAs), and the like); a transmitter 1305 and a receiver 1306, which may be coupled to an antenna or a communication port, for use in communicating with other apparatuses; and local storage unit (a.k.a., "data storage system") 1312, which may include one or more non-volatile storage devices (e.g., flash memory, hard disk, optical disk, etc.) and/or one or more volatile storage devices (e.g., volatile random access memory (RAM)). In embodiments where the DPS 1302 includes a programmable microprocessor, a computer program product (CPP) 1341 may be provided. CPP 1341 includes a computer readable medium (CRM) 1342 storing a computer program (CP) 1343 comprising computer readable instructions (CRI) 1344. CRM 1342 may be a non-transitory computer readable medium, such as, but not limited to, magnetic media (e.g., a hard disk), optical media (e.g., a DVD), memory devices (e.g., flash memory, volatile RAM), and the like. In some embodiments, the CRI 1344 of computer program 1343 is configured such that when executed by data processing system 1302, the CRI causes the apparatus to perform steps described herein (e.g., steps described above with reference to the flow charts). In other embodiments, the apparatus may be configured to perform steps described herein without the need for code. That is, for example, data processing system 1302 may consist merely of one or more ASICs. Hence, the features of the embodiments described herein may be implemented in hardware and/or software.

While various embodiments of the present disclosure are described herein (including the appendix), it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

The invention claimed is:

1. A method for delivering a dynamically generated media stream to a client, the media stream comprising a plurality of media segments including a first media segment and a second media segment, the method comprising:

receiving an indication to send to the client a manifest file, wherein the manifest file comprises information describing the media segments;

sending, to the client, the manifest file in response to receiving the indication to send to the client the manifest file;

after sending the manifest file to the client, receiving an indication to send to the client the first media segment; and in response to the indication to send to the client the first media segment, sending, to the client, a segmentation map for the first media segment, wherein the first media segment comprises an ordered set of fragments including a first fragment and a second fragment, and the segmentation map comprises: first fragment metadata comprising a first fragment identifier for use in accessing the first fragment from a server, second fragment metadata comprising a second fragment identifier for use in accessing the second fragment from a server, and ordering information identifying the ordering of the fragments within the set of fragments, including information indicating that the first fragment is ordered before the second fragment.

2. The method of claim 1, further comprising:

receiving an indication to send to the client the first fragment; and sending, to the client, the first fragment in response to receiving the indication to send to the client the first fragment.

3. The method of claim 2, wherein one or more of the indication to send to the client the manifest file, the indication to send to the client the first media segment, and the indication to send to the client the first fragment is generated by the server without client input.

4. The method of claim 1, wherein the indication to send to the client the first media segment is a request transmitted by the client, the request comprises information for identifying the first media segment, and the request further comprises an indicator indicating that the client supports a segmented mode.

5. The method of claim 4, further comprising determining to use a segmented mode to deliver the media segment, wherein the determination is based at least in part on the indicator.

6. The method of claim 5, wherein determining to use the segmented mode to deliver the first media segment is further based at least in part on whether the first media segment has been fully generated.

7. The method of claim 4, wherein a content of the manifest file is based on the indicator that the client supports a segmented mode, and the content of the manifest file that is based on the indicator comprises a hint regarding a time of resource availability for the plurality of media segments.

8. The method of claim 1, wherein the first fragment metadata further comprises one or more of:

first dependency information for the first fragment, the first dependency information indicating that the availability of the first fragment to be delivered from the server is dependent on one or more other fragments of the set, first position information including one or more of: a length of the first fragment, a start position of the first fragment in the media segment, and an end position of the first fragment in the media segment, and first fragment-level security information for use in verifying the integrity of the first fragment.

9. The method of claim 1, further comprising:

receiving, a part of the first media segment from a source dynamically generating the media stream, wherein the part of the first media segment corresponds to at least one of a media sample and a media application data unit; and packetizing the part of the first media segment according to a format, wherein the format is ISO Base Media File Format.

10. The method of claim 9, wherein the first fragment comprises media samples, and the second fragment comprises metadata associated with the media samples.

11. A server for delivering a dynamically generated media stream to a client, the media stream comprising a plurality of media segments including a first media segment and a second media segment, comprising:

a data storage system comprising a memory; and a data processing system comprising a processor, wherein the server is configured to:

receive an indication to send to the client a manifest file, wherein the manifest file comprises information describing the media segments;

send, to the client, the manifest file in response to receiving the indication to send to the client the manifest file;

after sending the manifest file to the client, receiving an indication to send to the client the first media segment; and in response to the indication to send to the client the first media segment, send, to the client, a segmentation map for the first media segment, wherein the first media segment comprises an ordered set of fragments including a first fragment and a second fragment, and the segmentation map comprises: first fragment metadata comprising a first fragment identifier for use in accessing the first fragment from a server, second fragment metadata comprising a second fragment identifier for use in accessing the second fragment from a server, and ordering information identifying the ordering of the fragments within the set of fragments, including information indicating that the first fragment is ordered before the second fragment.

12. A method, performed by a client, for receiving a dynamically generated media stream, the media stream comprising a plurality of media segments including a first media segment and a second media segment, the method comprising:

receiving a manifest file, wherein the manifest file comprises information for enabling the client to generate requests for the media segments;

processing the received manifest file;

after processing the manifest file, receiving a segmentation map for the first media segment, wherein the first media segment comprises an ordered set of fragments including a first fragment and a second fragment, and the segmentation map comprises: first fragment metadata comprising a first fragment identifier for use in accessing the first fragment from a first server, second fragment metadata comprising a second fragment identifier for use in accessing the second fragment from a server, and ordering information identifying the ordering of the fragments within the set of fragments, including information indicating that the first fragment is ordered before the second fragment; and receiving the first fragment.

13. The method of claim 12, further comprising:
prior to receiving the manifest file, sending a request for a manifest file;
after processing the manifest file and before receiving the segmentation map, sending a request identifying the first media segment.

14. The method of claim 13, wherein the request identifying the first media segment comprises an indicator indicating that the client supports a segmented mode.

15. The method of claim 14, wherein an application layer of the client assembles the first media segment based on the information in the segmentation map including the identity of the fragments, their provided offset in the file, or the sequence of fragments.

16. The method of claim 12, further comprising:
verifying the first fragment;
verifying the first media segment; and
decoding and playing the first fragment, wherein the decoding and playing the first fragment occurs after verifying the first fragment and before verifying the first media segment.

17. The method of claim 12, further comprising playing the first fragment, wherein playing the first fragment occurs prior to receiving other fragments of the media segment.

18. A client for receiving a dynamically generated media stream, the media stream comprising a plurality of media segments including a first media segment and a second media segment, the client comprising:
a data storage system comprising a memory; and
a data processing system comprising a processor, wherein the client is configured to:
receive a manifest file, wherein the manifest file comprises information for enabling the client to generate requests for the media segments;
process the received manifest file;
after processing the manifest file, receive a segmentation map for the first media segment, wherein the first media segment comprises an ordered set of fragments including a first fragment and a second fragment, and the segmentation map comprises: first fragment metadata comprising a first fragment identifier for use in accessing the first fragment from a first server, second fragment metadata comprising a second fragment identifier for use in accessing the second fragment from a server, and ordering information identifying the ordering of the fragments within the set of fragments, including information indicating that the first fragment is ordered before the second fragment; and
receive the first fragment.

19. A computer program product comprising a non-transitory computer readable medium storing a computer program comprising instructions which, when executed on at least one processor, cause the at least one processor to carry out the method according to claim 1.

* * * * *